(12) United States Patent
Eberl et al.

(10) Patent No.: US 8,425,920 B2
(45) Date of Patent: Apr. 23, 2013

(54) METHOD FOR INDUCING LYMPHOID TISSUE AND MODULATING INTESTINAL HOMEOSTASIS

(75) Inventors: Gerard Eberl, Paris (FR); Djahida Bouskra, Dugny (FR); Ivo Gomperts Boneca, Vitry Si Seine (FR); Christophe Brezillon, Vanves (FR)

(73) Assignee: Institut Pasteur, Paris (FR)

( * ) Notice: Subject to any disclaimer, the term of this patent is extended or adjusted under 35 U.S.C. 154(b) by 476 days.

(21) Appl. No.: 12/430,713

(22) Filed: Apr. 27, 2009

(65) Prior Publication Data

US 2010/0272646 A1   Oct. 28, 2010

(51) Int. Cl.
*A61K 39/02*   (2006.01)

(52) U.S. Cl.
USPC ........................................ 424/278.1

(58) Field of Classification Search ........................ None
See application file for complete search history.

(56) References Cited

U.S. PATENT DOCUMENTS

2005/0163764 A1*   7/2005   Medzhitov et al. ........ 424/93.45
2006/0084090 A1*   4/2006   Ferrero et al. ..................... 435/6

OTHER PUBLICATIONS

Bouskra et al. (Nature, 456:507-512, Nov. 2008).*
Schultz et al. (Clin. Diag. Lab. Immunol., 11:372-378, 2004).*
Mahadevan et al. (Gastroenterol., 124:1636-1650, 2003).*
Cukrowska et al. (Scand. J. Immuol., 55:204-209, 2002).*

* cited by examiner

*Primary Examiner* — Brian J Gangle
(74) *Attorney, Agent, or Firm* — Oblon, Spivak, McClelland, Maier & Neustadt, L.L.P.

(57) ABSTRACT

Methods and products for modulating the lymphoid system, especially intestinal homeostasis between intestinal lymphoid tissues and gut flora using ligands for NOD1 and/or CCR6.

14 Claims, 11 Drawing Sheets

METHOD FOR INDUCING LYMPHOID TISSUE AND MODULATING INTESTINAL HOMEOSTASIS

BACKGROUND OF THE INVENTION

1. Field of the Invention

Methods and products for regulating equilibrium or homeostasis between intestinal microflora and the immune system, especially via lymphoid tissue genesis associated with NOD1. Genesis or neogenesis of isolated lymphoid follicles (ILFs) using molecules that interact with NOD1 expressed on epithelial cells.

2. Description of the Related Art

Intestinal homeostasis between the intestinal microflora and the immune system is critical for efficient energy extraction from food and protection from pathogens by maintenance of a robust epithelial barrier. Homeostatic disruption can lead to an array of severe illnesses of major impact on public health, such as inflammatory bowel disease characterized by self-destructive intestinal immunity. However, the mechanisms regulating the equilibrium between the large bacterial flora and the immune system remain unclear.

After birth colonization of the intestines by commensal bacteria and other microorganisms evokes a response by the epithelial barrier and the immune system that induces recruitment of lymphocytes, maturation of lymphoid tissues, and production of IgA immunoglobulins. Intestinal lymphoid tissues generate flora-reactive IgA-producing B cells and include Peyer's patches, mesenteric lymph nodes, as well as numerous isolated lymphoid follicles (ILFS)[1,2]. Secondary lymphoid tissues, such as lymph nodes (LNs) and Peyer's patches (PPs), are induced to develop in the sterile environment of the fetus by lymphoid tissue inducer (LTi) cells[3]. After birth, hundreds of small clusters of LTi-like cells termed cryptopatches (CPs) form between crypts in the intestinal lamina propria[4]. During bacterial colonization, several lines of evidence indicate that CPs recruit B cells and develop into ILFs[5,6], recapitulating the fetal development of LNs and PPs[7]. However, in contrast to the programmed development of LNs and PPs, the formation of mature ILFs from CPs requires induction by the gut flora[1,8]. Furthermore, in mice that harbor an expanded bacterial flora as a consequence of a lack of IgA, ILFs are abnormally large and numerous[9]. Given the inducible nature of ILFs, it is possible that these lymphoid tissues play an essential role in the equilibrium between the gut flora and the immune system[7]. However, the components of the gut flora that induce the genesis of ILFs, the factors that induce the recruitment of B cells into CPs, and the impact of ILFs on the gut flora remain largely unknown.

Methods for modulating NOD1 activity are disclosed by Girardin, et al., U.S. Pat. No. 7,078,165 which describes NOD1 as a pathogen recognition molecule expressed by eukaryotic cells that senses Gram-negative bacteria via a peptidoglycan motif, muramyl tripeptide or MTP. Girardin proposes to use MTP-like molecules to modulate NOD1 activity in eukaryotic cells.

Nuñez, et al., U.S. Pat. No. 7,244,557, relates to NOD1 protein as an intracellular signaling molecule and describes screening methods for molecules that modulate NOD1 activity using cells expressing NOD1.

Sansonetti, et al., U.S. Pat. No. 7,396,812, describes a method for enhancing host immune responses by administering MTP-like molecules, such as GlcNAc-MurNAc-L-Ala-D-Glu-mesoDAP (MTP), MurNAc-L-Ala-D-Glu-mesoDAP, and L-Ala-D-Glu-mesoDAP.

Nucleotide-binding oligomerization domain containing 1 ("NOD1") is a gene found in humans and other mammals that encodes NOD1 protein. NOD1 protein contains a caspase activation and recruitment domain (CARD). Caspases or "cysteine-aspartic acid proteases" are a family of cysteine proteases that are involved in programmed cell death, apoptosis, cellular necrosis, and inflammation. Caspase recruitment domains are segments of proteins that interact with caspases and are found in a variety of different proteins, such as those involved in inflammation or apoptosis.

CCL20 is a small cytokine belonging to the CC chemokine family. It is known under various names including chemokine (C—C motif) ligand 20, liver activation regulated chemokine (LARC), or Macrophage Inflammatory Protein-3 (MIP3A). CCL20 is strongly chemotactic for different types of leukocytes and is implicated in the formation and function of mucosal lymphoid tissue, via chemoattraction of lymphocytes and dendritic cells towards the epithelial cells surrounding these tissues. CCL20 elicits its effects on its target cells by binding and activating chemokine receptor CCR6.

Murine β-defensin 3 (mBD3) is a defensin, one of a group of small cationic cysteine-rich cationic proteins found in both vertebrates and invertebrates. Beta-defensins exhibit broad spectrum antimicrobial activity against bacteria, fungi and enveloped viruses. They have molecular masses ranging from 2-6 kDa and have six to eight conserved cysteine residues. Whereas α-defensins are produced by phagocytes and Paneth cells, β-defensins are produced primarily by epithelial cells. Mouse β-defensin 3, the ortholog of human β-defensin 2, binds to (is a ligand of) CCR6; Biragyn, et al., *J Immunol.* Dec. 1, 2001; 167(11):6644-53. The structure of human β-defensin 2 (also known as DEFB2, DEFB4) is incorporated by reference to UniProtKB/Swiss-Prot O15263 (DEFB2_HUMAN) version 94, Mar. 3, 2009. The structure of murine β-defensin 3 is incorporated by reference to UniProtKB/Swiss-Prot Q9WTL0 (DEFB3_MOUSE), version 60, Mar. 3, 2009.

BRIEF SUMMARY OF THE INVENTION

The inventors have demonstrated that adaptive lymphoid tissues are generated by the interaction of bacterial products, such as Gram-negative peptidoglycans, with NOD1 bearing host cells. Genesis or neogenesis of adaptive lymphoid tissues, such as ILFs (isolated lymphoid follicles) contributes and promotes intestinal homeostasis between the host immune system and microorganisms. In the absence of ILFs, or when ILF numbers are disregulated, the composition of intestinal commensal microorganisms is profoundly altered. This can lead to disruption of intestinal homeostasis and subsequent development of disorders such as infectious diseases or inflammatory or autoimmune disorders.

The inventors have found that regulation and restoration of homeostasis can be achieved by the administration of full or partial agonists, such as NOD1 agonists, or alternatively by NOD1 antagonists or molecules that antagonize murine β-defensin (e.g., murine β-defensin 3 or human beta defensin 2) and/or the C—C motif chemokine ligand 20 (e.g., murine CCL20 or human CCL20) binding to CCR6. These molecules respectively can induce or inhibit genesis or neogenesis of adaptive lymphoid tissues, notably ILFs (isolated lymphoid follicles).

The inventors show that peptidoglycans from Gram-negative bacteria are necessary and sufficient to induce the genesis or neogenesis of ILFs (isolated lymphoid follicles) through recognition by the NOD1 innate receptor in epithelial cells, and β-defensin 3- and CCL20-mediated signaling through the chemokine receptor CCR6. Maturation of ILFs into large B cell clusters was found to require subsequent detection of bacteria by toll-like receptors and that the make-up of the intestinal bacterial community is profoundly altered in the absence of ILFs. The recognition of these processes permits control of intestinal homeostasis by modulating communication between commensal intestinal bacteria and the immune system to generate adaptive lymphoid tissues by means of specific receptor-ligand interactions.

One aspect of the invention is a method for modulating intestinal homeostasis in a subject, such as a mammal, by generating adaptive lymphoid tissue by administering to the subject an amount of one or more NOD1 ligands, and/or CCR6 ligands, such as murine β-defensin 3 and a CCL20, sufficient to induce or enhance the formation of ILFs in the subject compared to a control subject not administered the agent(s). Based on the inventors' discoveries, one preferred method to administer both a NOD1 ligand as well as or more CCR6 ligands, such as both β-defensin 2 and CCL20 to a human subject. This has the advantage of stimulating at two points in the activation pathway leading to formation of ILFs.

The NOD1 ligand may be a gram-negative bacterium or a molecule expressed by a Gram-negative bacterium, such as peptidoglycan or a fragment thereof. Chemical modified or synthetic peptidoglycans or their fragments are also contemplated. Such agents include mesoDAP-type peptidoglycan, muropeptide GMtetraDAP, *Escherichia coli* strain Nissle 1917, a component of *Escherichia coli* strain Nissle 1917, *Bacteroides*, and *Bacteroides* polysaccharide. Other agents include GanhydroMtetraDAP, TetraDAP, GMtriDAP, GanhydroMtriDAP, triDAP, meso-lanthioneine-type peptidoglycan, GMtetraLan (where Lan stands for meso-lanthionine), GanhydroMtetraLan, tetraLan, GMtriLan, and GanhydroMtriLan.

CCR6 ligands useful in the invention include a β-defensin falling in the genus of those corresponding to murine β-defensin 3 and human β-defensin 2, as well as C—C motif chemokine ligand 20, such as human CCL20 or murine CCL20. CCR6 bind portions of these molecules may also be employed. Preferably, in humans a ligand for human NOD1 and/or human β-defensin 2 and/or human CCL20 will be employed. Similarly, for other species, the corresponding ligands for those species will be employed, for example, in mice, murine β-defensin 3 and/or CCL20 ligands and ligands for murine NOD1 will be preferred.

The subject may be a neonate or a subject having an undeveloped or naïve immune system or a subject having a reduced number of ILFs compared to an otherwise similar normal subject. A subject may be one that has an innate immune defect, such as one who does not produce, or produces defective, IgA or other secretory antibodies or secretory components. Subjects having abnormally low or reduced numbers of ILFs compared to normal subjects or average values for normal subjects may be treated.

Alternatively, the subject may have an immune system that has lost homeostasis by drug treatment, disease, or surgery. Gastrointestinal and intestinal diseases and disorders that may be treated include duodenal, jejunal, ileal, cecal, colonic, bowel and rectal disorders and diseases requiring adjustment of homeostasis to enhance levels of immunity associated with ILFs. These include enteritis, gastroenteritis, dysentery, enterocolitis, viral, bacterial and parasitic infections. HIV enteropathy, pneumatosis cystoides intestinalis, intestinal neoplasms, intestinal polyposis, malabsorbtion syndrome, intestinal obstruction, intestinal fistula, intestinal atresia, intestinal perforation, mesenteric vascular occlusion, protein-losing enteropathy, and Zollinger-Ellison Syndrome. Subjects who have been exposed to environmental influences or agents that disrupt intestinal function and flora may be treated. These include those exposed to ionizing radiation, chemical agents, drugs, such as antibiotics that affect enteric microbial flora or intestinal function. Such subjects include those treated with or exposed to a chemical agent, drug, or antibiotic that disrupts or alters the normal composition of intestinal flora or reduces the number of ILFs compared to otherwise similar subjects not exposed to the agent or antibiotic.

Surgical patients, such as those who have undergone gastrointestinal surgery, bariatric surgery, or appendectomy can benefit especially when intestinal homeostasis has been disrupted or disregulated by these procedures.

Administration of ligands for NOD1 or CCR6 ligands may be oral, enteral or parenteral or any other suitable route including those listed in the U.S. FDA, CDER, Data Standards Manual "Routes of Administration", CDRG-00301, Version 004, which is hereby incorporated by reference. Dosage forms include any suitable form described by the U.S. FDA CDER Data Standards Manual C-DRG-00201, Version 08, which is hereby incorporated by reference.

In another aspect, a method for down-regulating the generation of adaptive lymphoid tissue is contemplated inhibiting or suppressing the generation of adaptive lymphoid tissue by administering to a subject, such as a human or non-human mammal, in need thereof an amount of at least one agent selected from the group consisting of an antagonist of an NOD1 ligand, an antagonist of a CCR6 ligand such as an antagonist to β-defensin 3, or an antagonist of CCL20, sufficient to reduce or inhibit the formation of ILFs in said host compared to a control subject not administered said agent(s). The antagonist may be an antibody or antigen-binding fragment of an antibody, such as Fab or Fab'2, that binds to an NOD1 ligand, or CCR6 ligand, such as β-defensin 3, or CCL20 or a soluble receptor, such as soluble NOD1, or CCR6 receptor.

The antagonist may be a gram-negative bacterium or a molecule expressed by a gram-negative bacterium, such as peptidoglycan or a chemically modified or synthesized peptidoglycan like molecule that exhibits antagonism or the ability to block stimulation by an NOD1 ligand. Examples of antagonistic peptidoglycan-like agents include insoluble peptidoglycan, soluble MurNAc pentapeptides lack the ability to stimulate Nod1, or peptidoglycans from bacteria that do not (effectively stimulate NOD1.

Subjects to be treated using antagonists that inhibit NOD1 or CCR6 activation would be those generally requiring a down-regulation of intestinal immunity to restore homeostasis, such as those having an inflammatory gastrointestinal disorder or disease or a gastrointestinal autoimmune disease or disorder, such as inflammatory bowel disease, scleroderma, and autoimmune phenomena associated with intestinal disorders or diseases.

The NOD1 or CCR6 antagonist may compete with or interfere with the binding an NOD1 ligand, such as an antibody or antibody fragment that binds either to the NOD1 ligand or to NOD1. A soluble NOD1 receptor may also be used to competitively inhibit NOD1 activation.

Similarly, an antagonist may be an antibody or antibody fragment that binds to CCR6, a CCR6 ligand, or a soluble CCR6 receptor which inhibits activation of CCR6 by a CCR6 ligand. An example, would be an antibody or antibody fragment that binds to a β-defensin or C—C motif chemokine ligand 20. For a human subject an antagonist may be an antibody or antibody fragment that binds to human CCR6 or which binds to human β-defensin 2 or to human CCL20. Subjects in need such a method may include those having an inflammatory gastrointestinal disorder or disease or a gastrointestinal autoimmune disease or disorder.

The invention is also directed to methods for identifying an agent that restores homeostasis in the gut comprising determining whether an agent is a NOD1 ligand, or a CCR6 ligand, determining whether said agent affects ILF formation, and optionally assessing the effect of the agent on the composition of intestinal microbial populations or on the levels of gastrointestinal immune factors. For example, this method may involve administering at least one agent to a mammal and determining whether said agent binds to NOD1, and/or CCR6, and measuring the number of ILFs formed compared to a control mammal not administered said agent; wherein formation of an increased number of ILFs compared to the control is indicative of an agent, such as an NOD1 or CCR6 activator or agonist, that can modulate homeostasis by increasing host immune responses, and formation of a decreased number of ILFs compared to the control is indicative of an agent that can modulate homeostasis by reducing host immune responses, e.g., by antagonizing NOD1 or CCR6 activation.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 4:
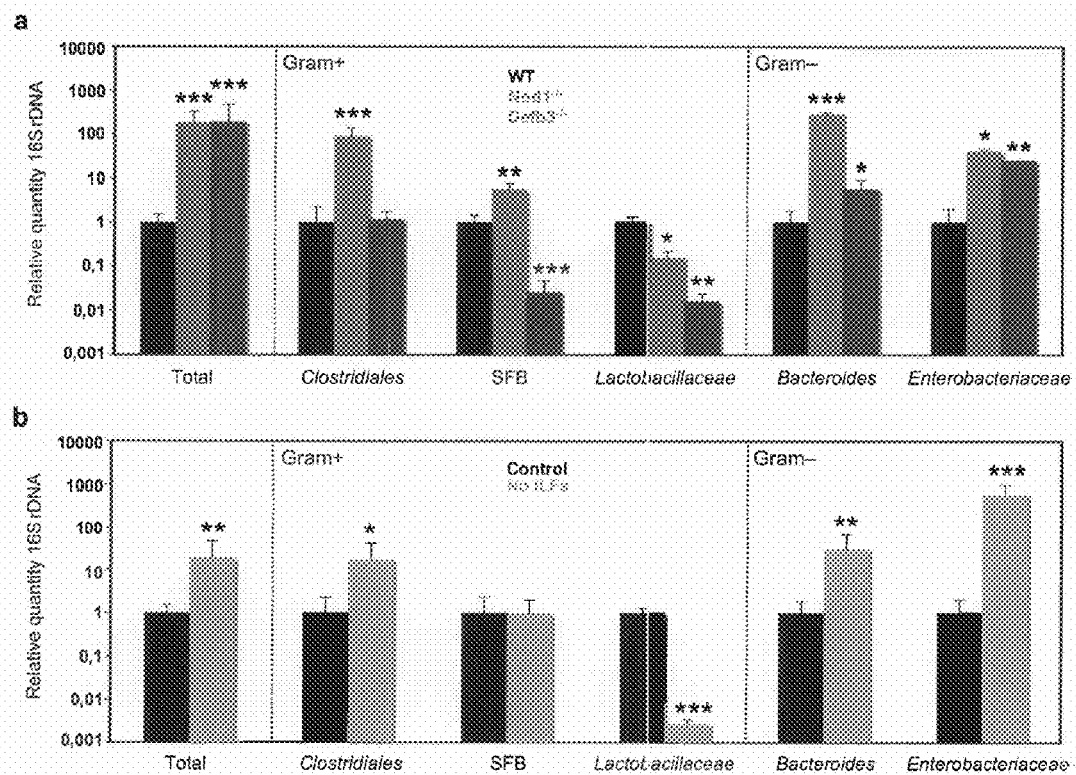
FIGS. 4(a) and (b). The impact of the CP-ILF system on the commensal flora. a,b, Quantification by qPCR of total bacterial 16S rDNA, as well as of 16S rDNA from major groups of mouse intestinal commensals present in the ileal biofilm of wild type, Nod1$^{-/-}$ and Defb3$^{-/-}$ mice (a) or of mice that lack ILF but have a normal set of LNs and PPs (treated with LTβR-Ig fusion protein after birth), or in control mice (treated with human IgG1) (b). Data are normalized to values obtained in wild-type mice or control-treated mice. Error bars, s.d.*P<0.05, P<0.01, *P<0.001, unpaired t test, as compared to wild type or control-treated mice. 3-4 mice per group were analyzed. All mice were bred in the same room of the mouse facility.

| | Supplementary Table | 16S rDNA-specific primers used in this study (FIG. 4)[1] | | | |
|---|---|---|---|---|---|
| Group | Taxonomic rank[2] | Genera included[3] | Phylum | Primer | Sequence (5' to 3') |
| Bacteria | Kingdom | All | | UniF340 | ACTCCTACGGGAGGCAGCAGT (SEQ ID NO: 1) |
| | | | | UniR514 | ATTACCGCGGCTGCTGGC (SEQ ID NO: 2) |
| Clostridiales | Order | Clostridium | Firmicutes[4] | UniF338 | ACTCCTACGGGAGGCAGC (SEQ ID NO: 3) |
| | | Eubacterium | | C.cocR491 | GCTTCTTAGTCAGGTACCGTCAT (SEQ ID NO: 4) |
| | | Epulopiscium | | | |
| | | Dorea | | | |
| | | Ruminococcus | | | |

-continued

Supplementary Table | 16S rDNA-specific primers used in this study (FIG. 4)[1]

| Group | Taxonomic rank[2] | Genera included[3] | Phylum | Primer | Sequence (5' to 3') |
|---|---|---|---|---|---|
| SFB[5] | Genus | SFB | *Firmicutes* | SFB736F | GACGCTGAGGCATGAGAGCAT (SEQ ID NO: 5) |
| | | | | SFB844R | GACGGCACGGATTGTTATTCA (SEQ ID NO: 6) |
| *Lactobacillaceae* | Family | *Lactobacillus* | *Firmicutes* | LabF362 | AGCAGTAGGGAATCTTCCA (SEQ ID NO: 7) |
| | | *Pediococcus* | | LabR677 | CACCGCTACACATGGAG (SEQ ID NO: 8) |
| *Bacteroides* | Genus | *Bacteroides* | *Bacteroidetes* | BactF285 | GGTTCTGAGAGGAAGGTCCC (SEQ ID NO: 9) |
| | | | | UniR338 | GCTGCCTCCCGTAGGAGT (SEQ ID NO: 10) |
| *Enterobacteriaceae* | Family | *Escherichia* | *Proteobacteria* | Uni515F | GTGCCAGCAGCCGCGGTAA (SEQ ID NO: 11) |
| | | *Salmonella* | | Ent826R | GCCTCAAGGGCACAACCTCCAAG (SEQ ID NO: 12) |
| | | *Yersinia* | | | |

[1] All primers have been listed and described previously by Barman et al.[1].
[2] A reminder of the hierarchy of the taxonomic ranks from highest to lowes kingdom, phylum. class, order, family, genus, species.
[3] Listed are only the genera detected by the primers, based on the genome sequences available in the NCBI database.
[4] *Firmicutes* are Gram+, whereas *Bacteroidetes* and *Proteobacteria* are Gram−.
[5] The genus "segmented filamentous bacteria" belongs to the class *Clostridia*[2].

Figure 5:
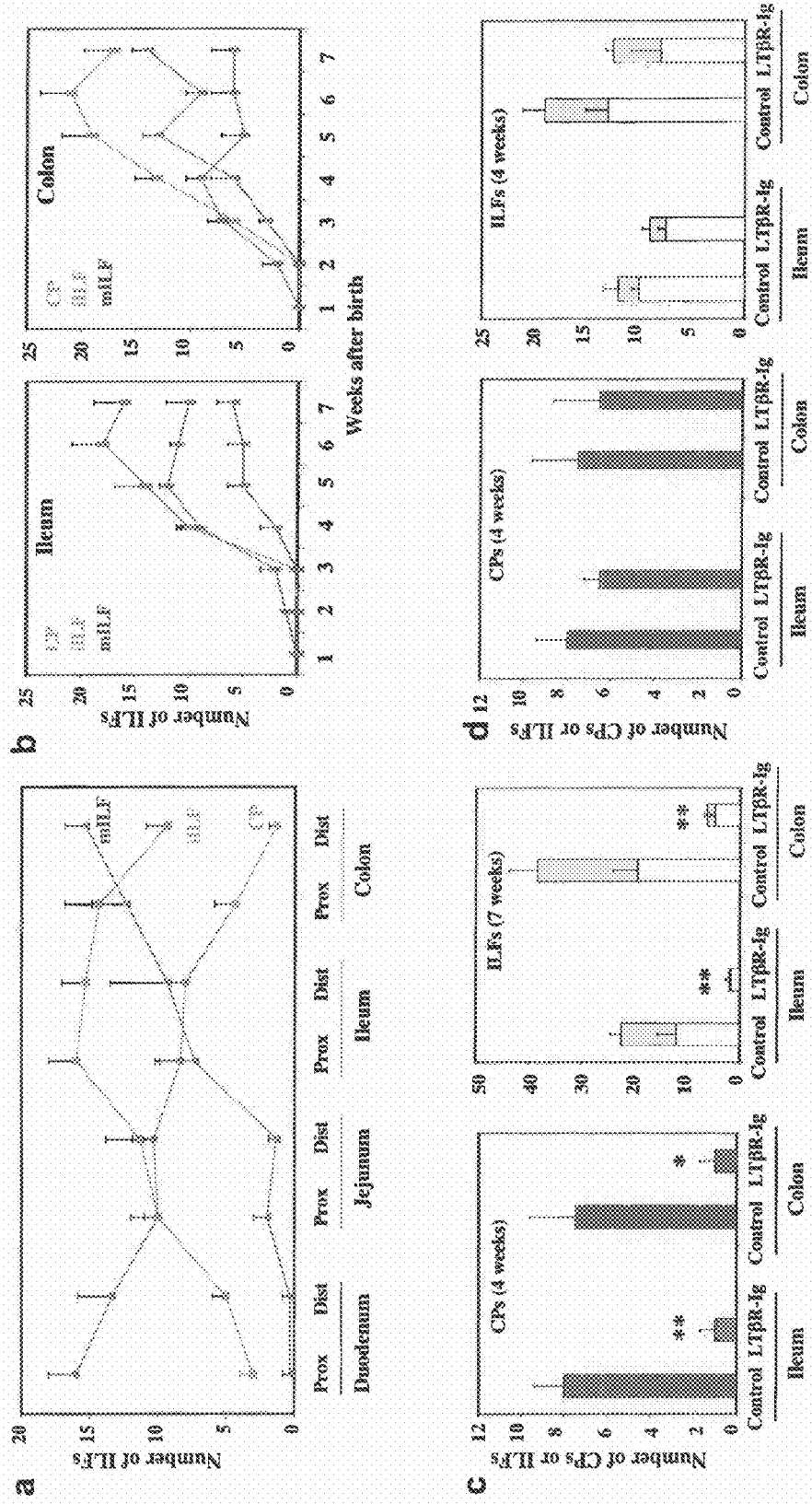

FIG. 5: Development of the CP-ILF system. a, The number of CPs, iILFs and mILFs in the intestine of 6-8 weeks old Rorc(γt)-Gfp$^{TG}$ mice. Fragments of 2 cm in length were cut from different regions of the intestine, cut, opened, fixed and frozen as flat "membranes". Ten to twenty sections were cut through the whole thickness of flat intestine, stained for GFP, CD45 and B220, and CPs and ILFs were counted. Because microscopic quantification of CPs and ILFs over the whole length of the intestine is extremely time and work expensive {Pabst, 2005 #36; Pabst, 2006 #41}, we restricted further quantification of CPs and ILFs to the distal ileum and the colon where significant numbers of iILFs and mILFs develop. b, The number of CPs, iILFs and mILFs were counted in 2 cm of distal ileum and 2 cm of proximal colon from 1 week to 7 weeks old Rorc(γt)-Gfp$^{TG}$ mice. c, Rorc(γt)-Gfp$^{TG}$ mice were injected with human IgG1 (control) or LTβR-Ig fusion protein from birth to 2 weeks of age, and the development of CPs and ILFs was assessed at 4 weeks and 7 weeks of age, respectively, in 3 mice per group. Error bars, s.d. *P<0.01, **P<0.001, unpaired t test, as compared to control. d, Pregnant Rorc(γt)-Gfp$^{TG}$ mice were injected with human IgG1 (control) or LTβR-Ig fusion protein 2 weeks after conception until birth. CPs and ILFs were then counted in 4 weeks old mice.

Figure 6:
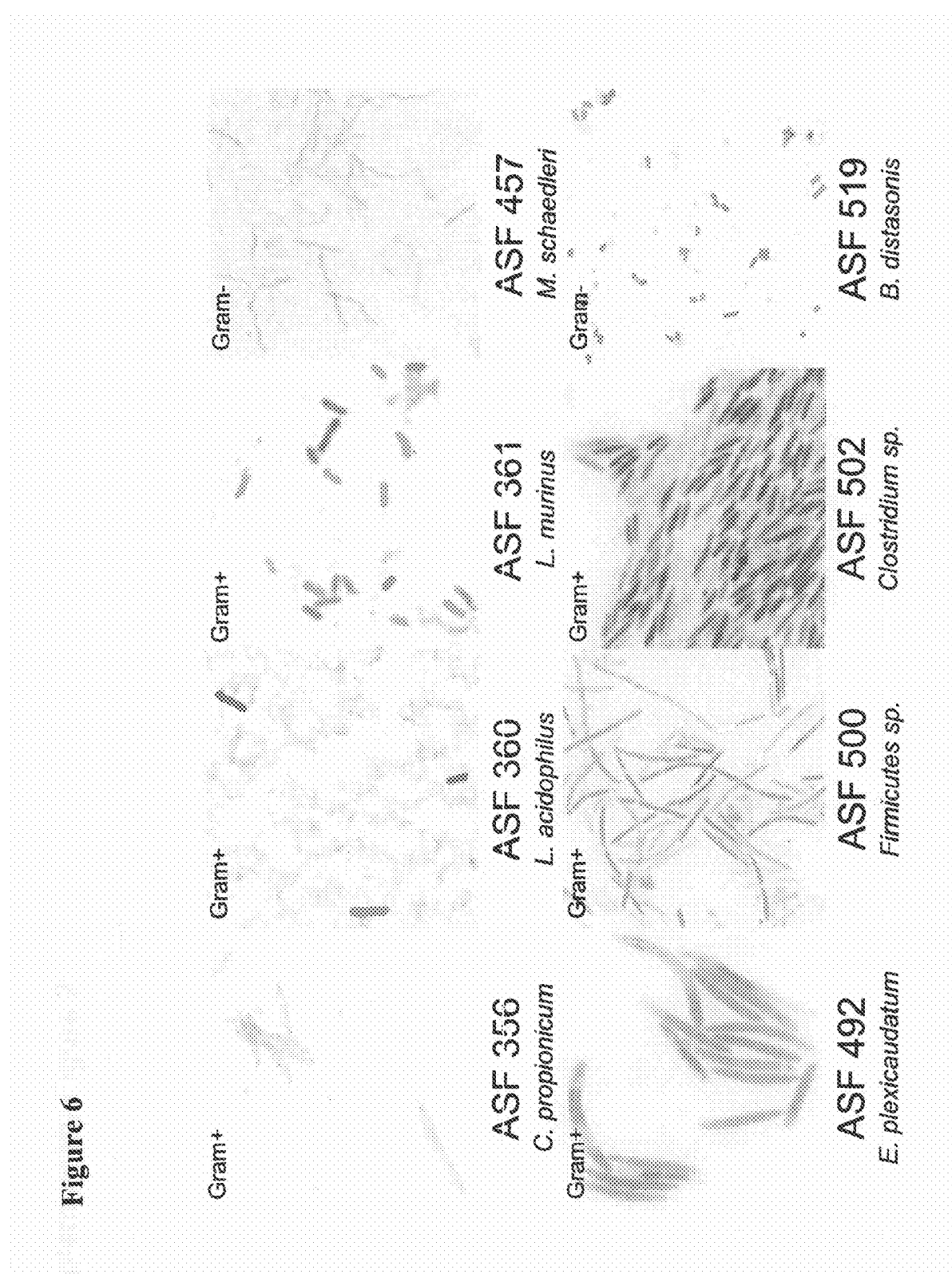

FIG. 6: Members of the altered Schaedler's cocktail. Gram coloration of the 8 Altered Schaedler Flora (ASF) strains from colonies isolated on Schaedler's agar. Gram+ strains include the fusiform-shaped anaerobes *Clostridium propionicum* (ASF 356), *Eubacterium plexicaudatum* (ASF 492), *Firmicutes* sp. (ASF 500) and *Clostridium* sp. (ASF 502), and the facultative anaerobes *Lactobacillus acidophilus* (ASF 360) and *Lactobacillus murinus* (ASF 361). Gram− strains include the spiral-shaped anaerobe *Mucispirillum schaedleri* (ASF 457) and the rod-shaped anaerobe *Bacteroides distasonis* (ASF 519).

Figure 7:
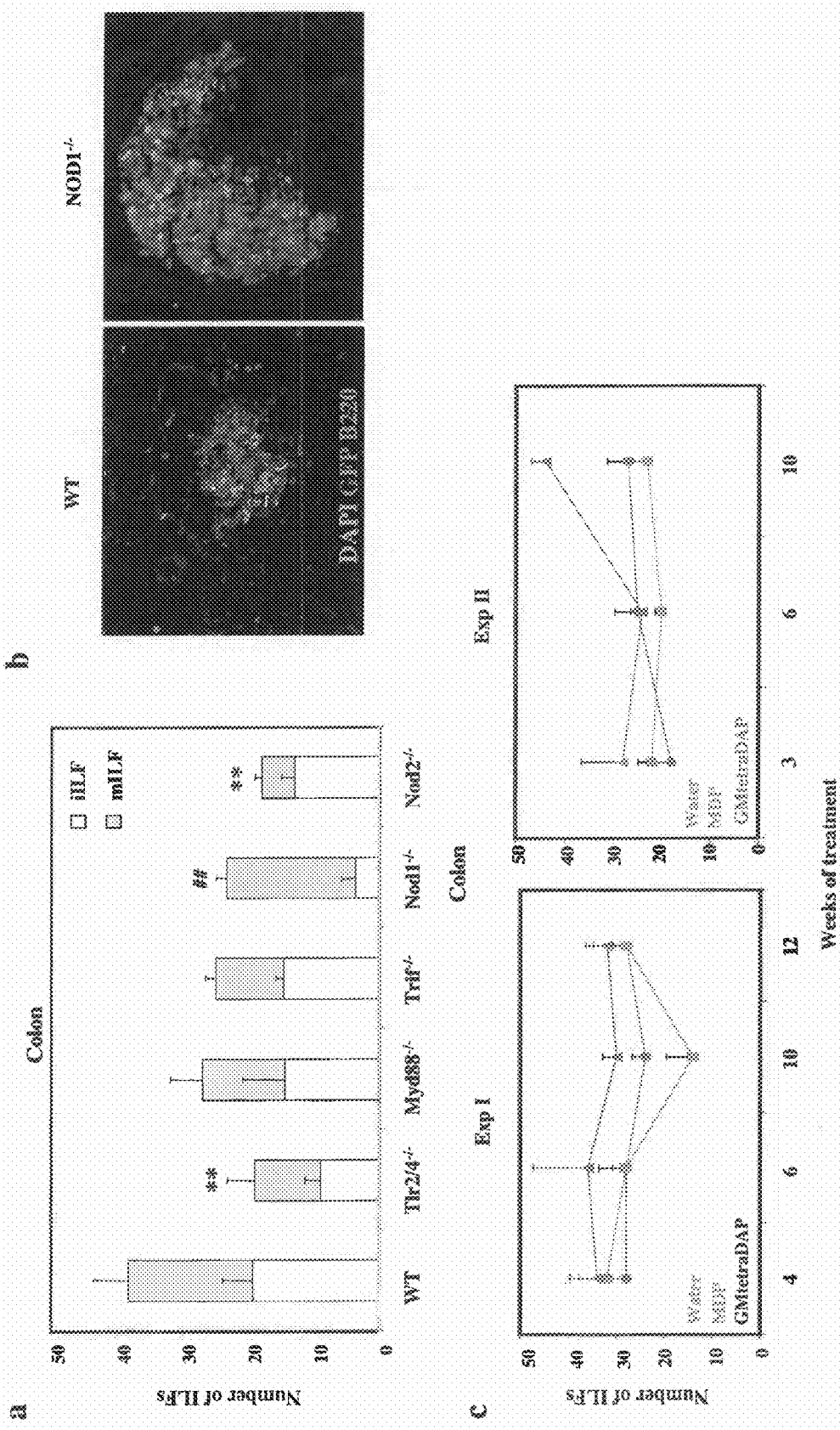

FIG. 7: The role of NOD1 and peptidoglycans in the formation of colonic ILFs. a, The number of iILFs and mILFs were counted in the proximal colon from wild type or mutant mice. Error bars, s.d. **P<0.01, unpaired t test, total numbers of ILFs as compared to wild type (WT) mice, and ##P<0.01, numbers of iILFs as compared to wild type (WT) mice. b, ILFs in sections from the colon of Nod1$^{+/-}$×Rorc(γt)-Gfp$^{TG}$ (WT) mice or Nod1$^{-/-}$×Rorc(γt)-Gfp$^{TG}$ mice were stained as indicated. In NOD1-deficient mice, a majority of ILFs were hyperplasic. Original magnification 200×. c, Germ free mice were given MDP or GMtetraDAP in the drinking water from 2 weeks of age (experiment I) or from birth (experiment II), and total ILFs were counted in the proximal colon after different periods of time. ILFs were counted in 2-4 mice per group.

Figure 8:
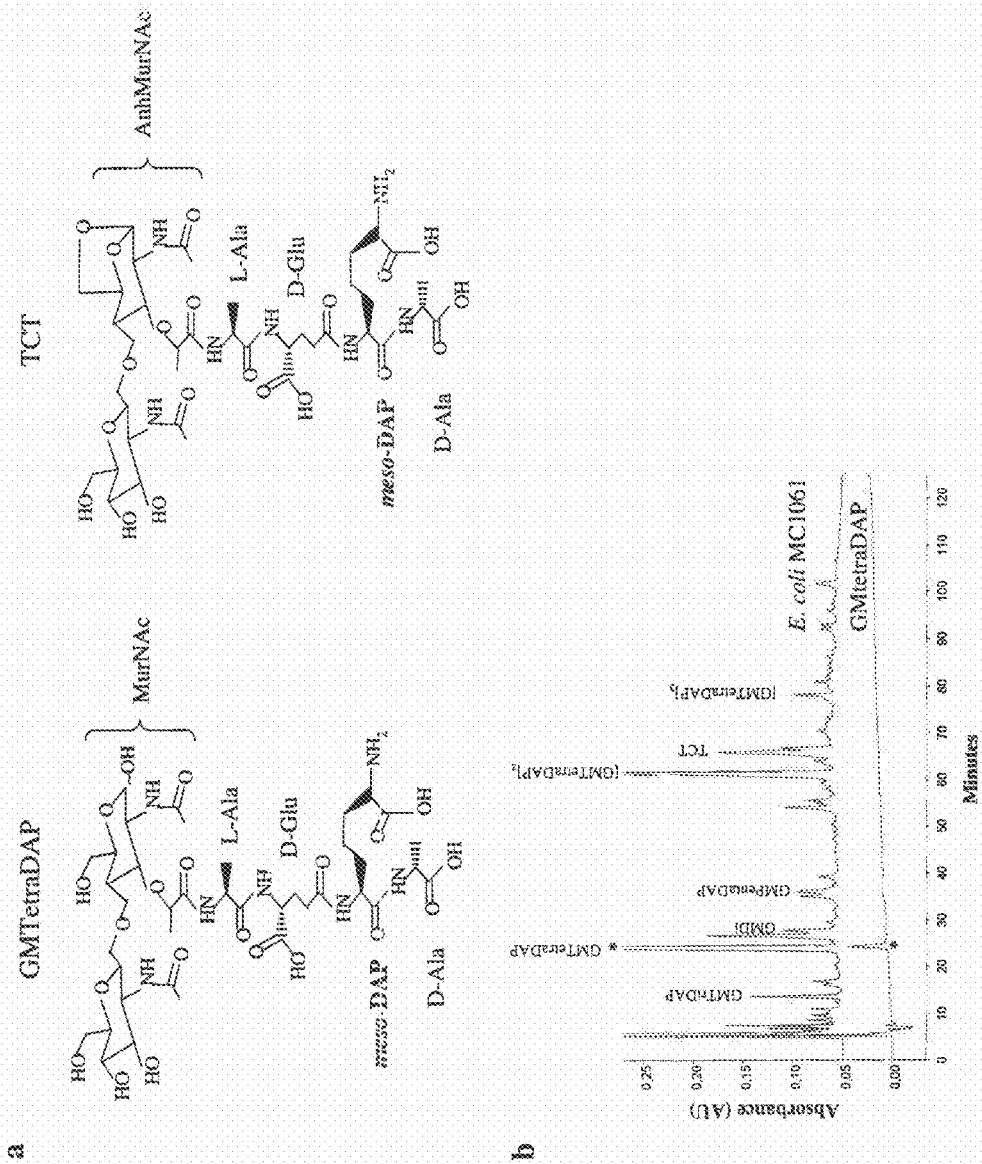

FIG. 8: Structure and purification of GMtetraDAP. a, Comparison of the chemical structures of the NOD1 ligands GMtetraDAP and TCT. b, Reverse Phase HPLC analysis of the entire range of muropeptides of *E. coli* MC1061. Major muropeptides are indicated above the corresponding peaks. Given the large amounts of GMtetraDAP produced in comparison to TCT, only GMtetraDAP was purified and used in our experiments indicates the peak corresponding to the GMtetraDAP that was purified from the PGN of *E. coli* MC 1061. The purity of GMtetraDAP was assayed by HPLC analysis, and the chemical nature of the purified GMtetraDAP was confirmed by MALDI-TOF mass spectrometry ([M+Na]$^+$ 944,3890 m/z) and post source decay-MALDI-TOF MS/MS (major fragmentation [M+Na]$^+$ ions: 873.3710, 741.3260, 701.3059 and 572.2461 m/z).

Figure 9:
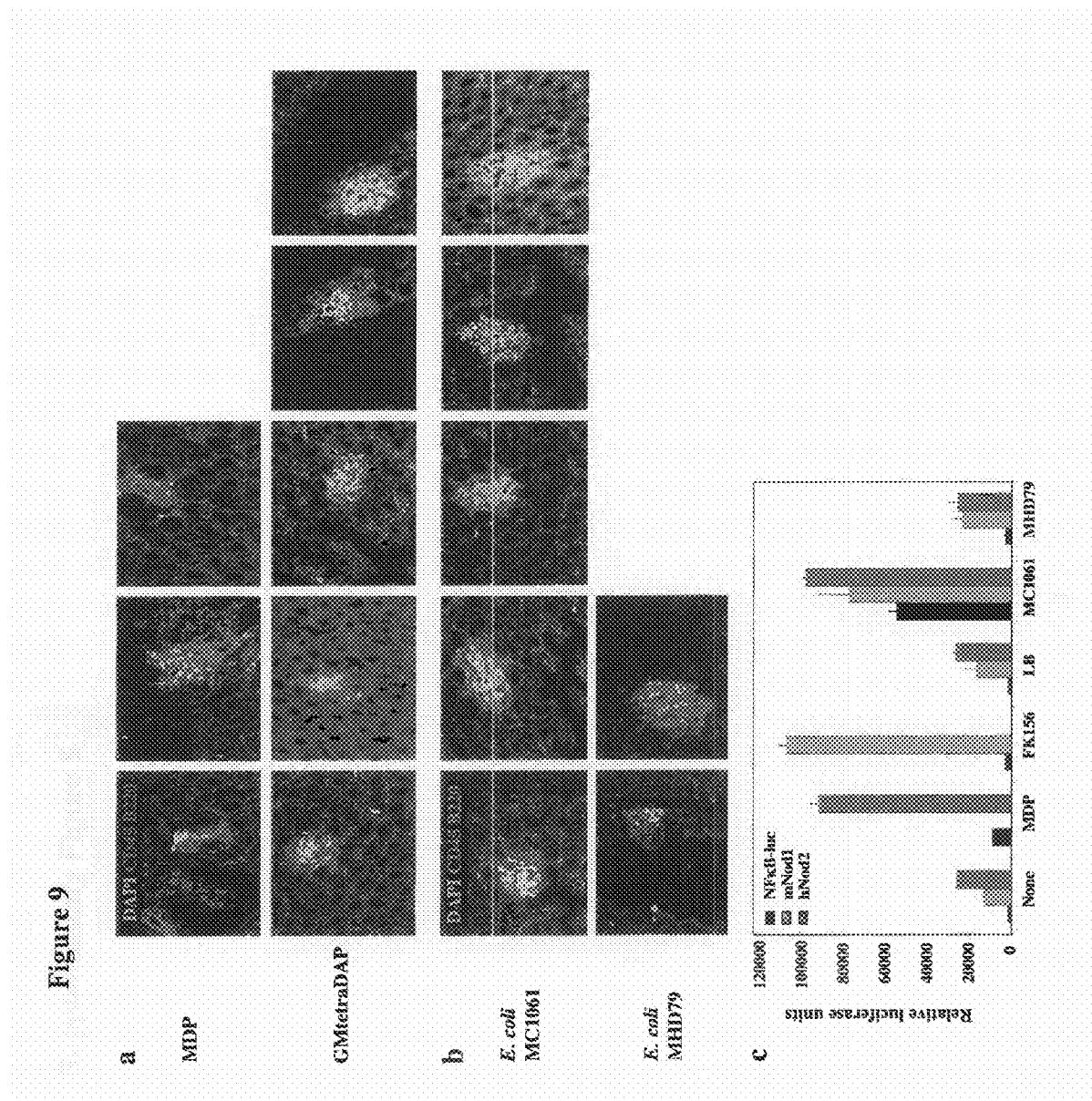

FIG. 9: The induction of ileal ILFs by GMtetraDAP. a, ILFs in sections from the ileum of 8 weeks old germ free mice that received MDP or GMtetraDAP in the drinking water from birth. In GMtetraDAP-treated mice, ILFs were numerous and showed some level of follicular organization. Original magnification 200×. b, ILFs in sections from the ileum germ free mice colonized by *E. coli* wild type strain MC 1061 or its isogenic mutant MHD79 impaired in PGN turnover and release of GMtetraDAP and TCT. In mice reconstituted with wild type but not mutant *E. coli*, ILFs were numerous and well organized. Original magnification 200×. c, The *E. coli* mutant MHD79 sheds no detectable amounts of NOD1 or NOD2 ligands. HEK293 cells, expressing endogenous human NOD1, were transfected with a plasmid carrying a luciferase reporter controlled by 5 NK-κB responsive elements, as well as a plasmid encoding β-galactosidase, alone or together with plasmids encoding mouse NOD1 or human NOD2. These cells were then cultured in the absence or presence of the NOD2 ligand MDP, the murine NOD1 ligand FK156, LB broth, or supernatant from cultures of *E. coli* wild-type MC 1061 or mutant MHD79. Luciferase activity was normalized to β-galactosidase activity. It has to be noted that MC1061 also releases ligands of human NOD1, and therefore induce luciferase expression in HEK293 cells transfected with the NF-κB-driven luciferase reporter alone.

Figure 10:
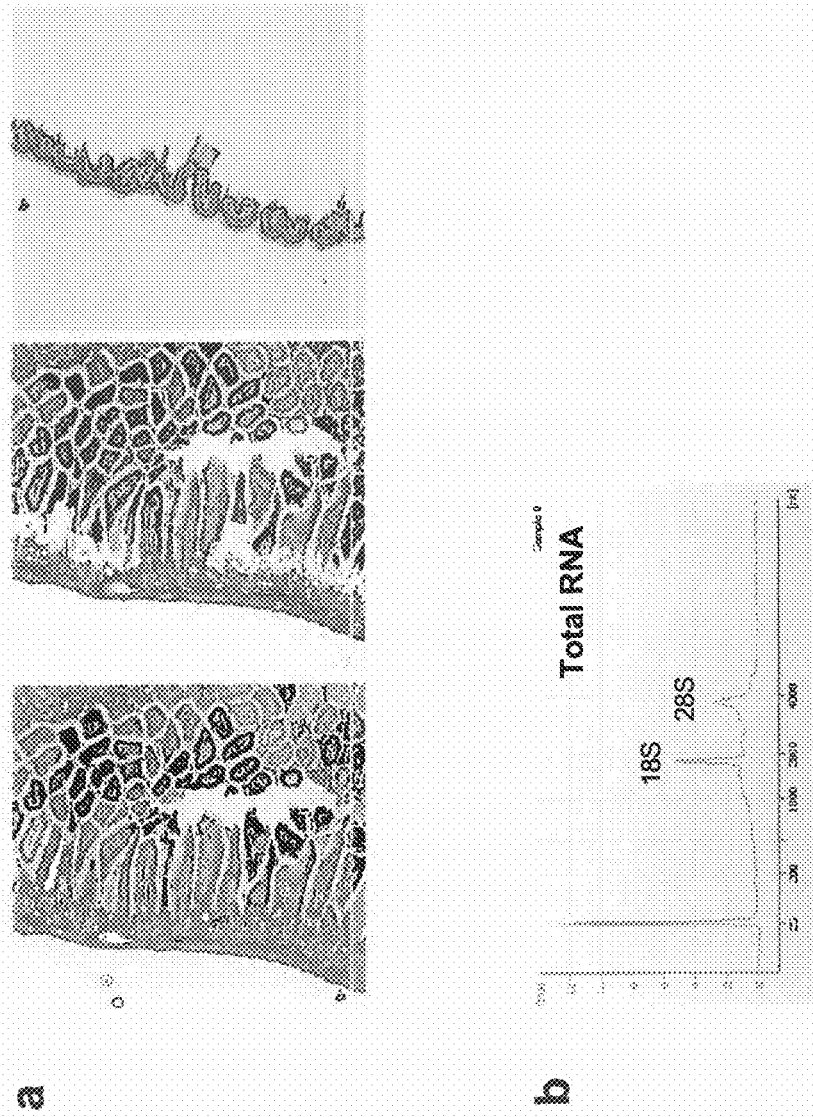

FIG. 10: Laser capture microdissection of ileal crypts. a, Sections of wild type ileum were briefly labeled with Histogen and microdissected. Shown are Histogen-labeled sections before and after microdissection, and the microdissected tissue fragment. Given the diameter (approximately 20 μm) of the infrared laser used to cut the tissue and the effective diameter of microdissected fragments, it is possible that both epithelial cells and contiguous cells from the lamina propria, such as DCs and macrophages, were isolated. Original magnification 50×. b, Analysis of purified total RNA from microdissected tissue fragments. Prominent pics of 18S and 28S ribosomal RNA indicate good RNA quality.

Figure 11:
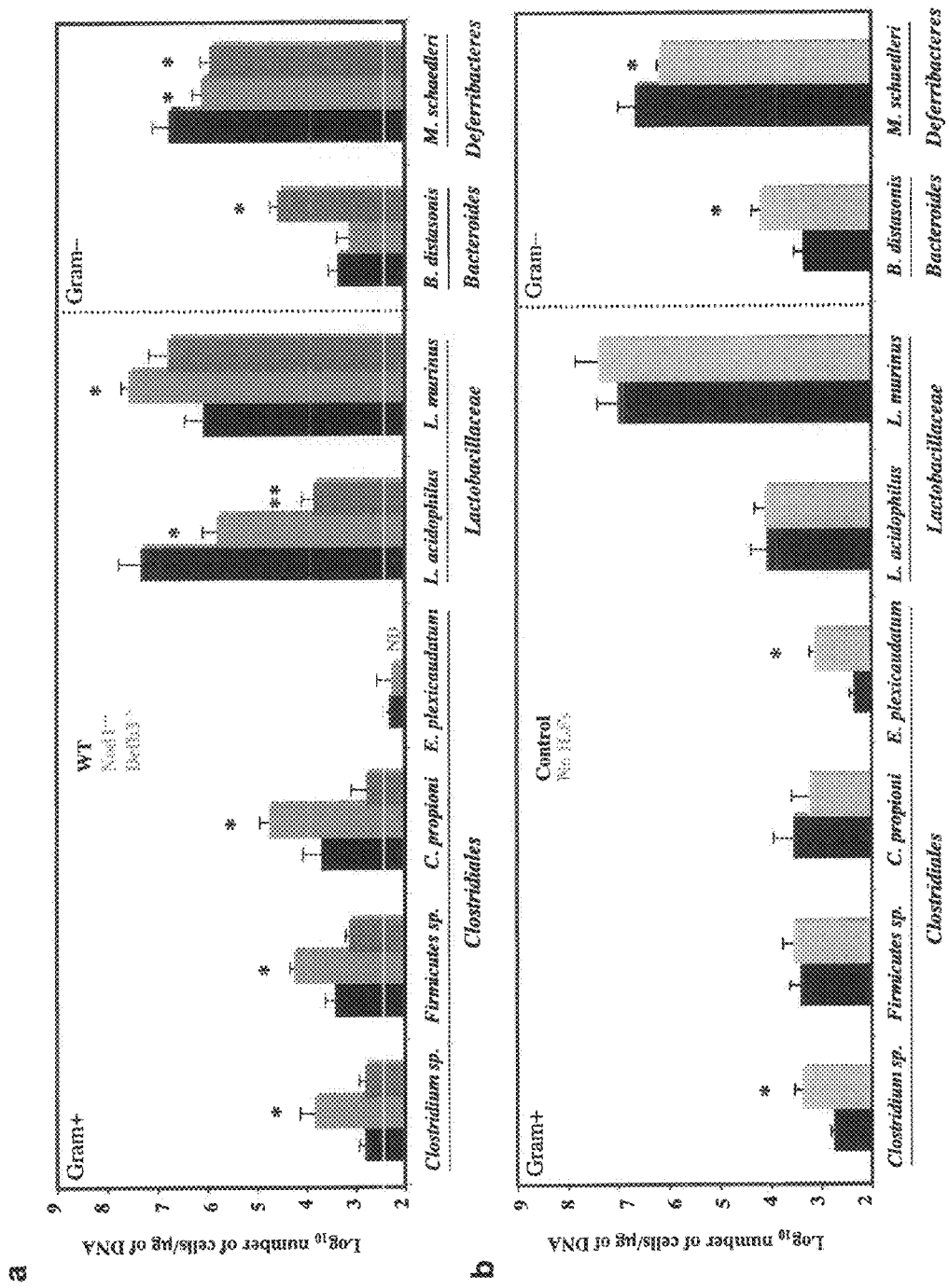

FIG. 11: The impact of the CP-ILF system on ASF strains. Quantification by qPCR of the 16S rDNA of ASF strains present in the ileal biofilm of wild type, Nod1$^{-/-}$ and Defb3$^{-/-}$ mice (a) or of LTβR-Ig-treated mice (b). Absolute numbers of bacterial cells are calculated with standard curves established by qPCR on rDNA-encoding reference plasmids, and are normalized to the quantity of DNA purified from intestinal biofilms. *C. propioni* is *C. propionicum*. Three to four mice per group were examined in independent experiments. All mice were bred in the same room of our mouse facility. ND, not detected. Error bars, s.d. *$P<0.05$, **$P<0.01$, unpaired t test, as compared to wild type or control-treated mice.

DETAILED DESCRIPTION OF THE INVENTION

The term "NOD1" refers to "Nucleotide-binding oligomerization domain containing 1". NOD1 protein contains a caspase activation and recruitment domain (CARD). A reference human sequence is given by version 81 (Mar. 3, 2009) as UniProtKB/Swiss-Prot Q9Y239 (NOD1_HUMAN). Murine and porcine reference sequences are described, respectively, by UniProtKB/Swiss-Prot Q8BHB0 (NOD1_MOUSE) (given by version 58, Mar. 24, 2009), and UniProtKB/TrEMBL B0FSM7 (B0FSM7PIG)(version 9, Feb. 10, 2009). Other mammalian proteins functionally corresponding to these NOD1 sequences are also encompassed.

"CCR6" refers to the class of molecules structurally and functionally similar to murine and human CCR6. Examples include murine CCR6 and human CCR6. Information including gene and protein structure and function information about human CCR6 is incorporated by reference to UniProtKB/Swiss-Prot P51684 (CCR6_HUMAN) (version 90, Mar. 24, 2009); and that for mouse CCR6 is incorporated by reference to UniProtKB/Swiss-Prot O54689 (CCR6_MOUSE)(version 69, Mar. 24, 2009).

CCR6 from other animals, such as non-human and non-murine mammals and birds that bind to the β-defensin or CCL20 molecules for the same species and share structural similarity, e.g, 99%, 95%, 90%, 80%, 70%, 60% with said murine and human β-defensins are also encompassed.

"Beta-defensin corresponding to murine β-defensin 3 and human β-defensin 3" refers to the class of molecules structurally and functionally similar to these two murine and human defensins. Corresponding β-defensins from other animals, such as non-human and non-murine mammals and birds, including chickens that bind to the CCR6 molecule for the same species and share structural similarity, e.g., 99%, 95%, 90%, 80%, 70%, 60% with said murine and human β-defensins are also encompassed. Information including gene and protein structure and function information about human beta-defensin 2 is incorporated by reference to UniProtKB/Swiss-Prot O15263 (DEFB2_HUMAN)(version 94, Mar. 3, 2009); that for murine beta-defensin 3 is incorporated by reference to UniProtKB/Swiss-Prot Q9WTL0 (DEFB3_MOUSE)(version 60, Mar. 3, 2009).

"C—C motif chemokine ligand 20 or CCL20" refers to the class of molecules in animals, such as mammals and birds, that corresponds to murine CCL20 and human CCL20. These molecules will bind to the CCR6 molecule from the same species and exhibit, such as 99%, 95%, 90%, 80%, 70%, 60% structural similarity, with murine or human CCL20 molecules. Information including gene and protein structure and function information about human CCL20 is incorporated by reference to UniProtKB/Swiss-Prot P78556 (CCL20_HUMAN)(version 90, Mar. 3, 2009); that for murine CCL20 is incorporated by reference to UniProtKB/Swiss-Prot O89093 (CCL20_MOUSE).

Other mammalian and avian molecules falling within the NOD1, CCR6, CCL20 and β-defensin genuses described above are encompassed, including those from domestic animals, pets, such as cats and dogs, livestock animals, such as cattle, goats, sheep, and pigs, and birds, such as chickens, turkeys, ducks and geese. Restoration or maintenance of intestinal homeostasis, which is critical for efficient energy extraction from food and for protection from pathogens, is important in economically important livestock to improve productivity by providing healthier, higher weight, and more productive livestock. Adult, weaning, and neonate livestock may be treated using the methods herein.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Alternatively, the molecule of interest—NOD1, CCR6, β-defensin or CCL20—of the present invention may be encoded by a nucleic acid sequence which hybridizes under stringent conditions with the nucleic acid sequence encoding the corresponding murine or human protein. Stringent conditions are known to those in the art and may include, for example, hybridization followed by washing in 5×SSC at a temperature ranging from 50° to 68° C.

The inventors have demonstrated the reciprocal regulation of the intestinal bacterial flora and the ILFs (isolated lymphoid follicles), and the role of the CP-ILF (cryptopatch-ILF) system in intestinal homeostasis. Modulation of the CP-ILF system through the nuclear receptor RORγt expressed by CP cells, or administration of NOD1 ligands or Gram-negative probiotics expressing and secreting high levels of NOD1 ligands, may contribute to re-establish normal intestinal homeostasis during intestinal pathology.

Figure 1:
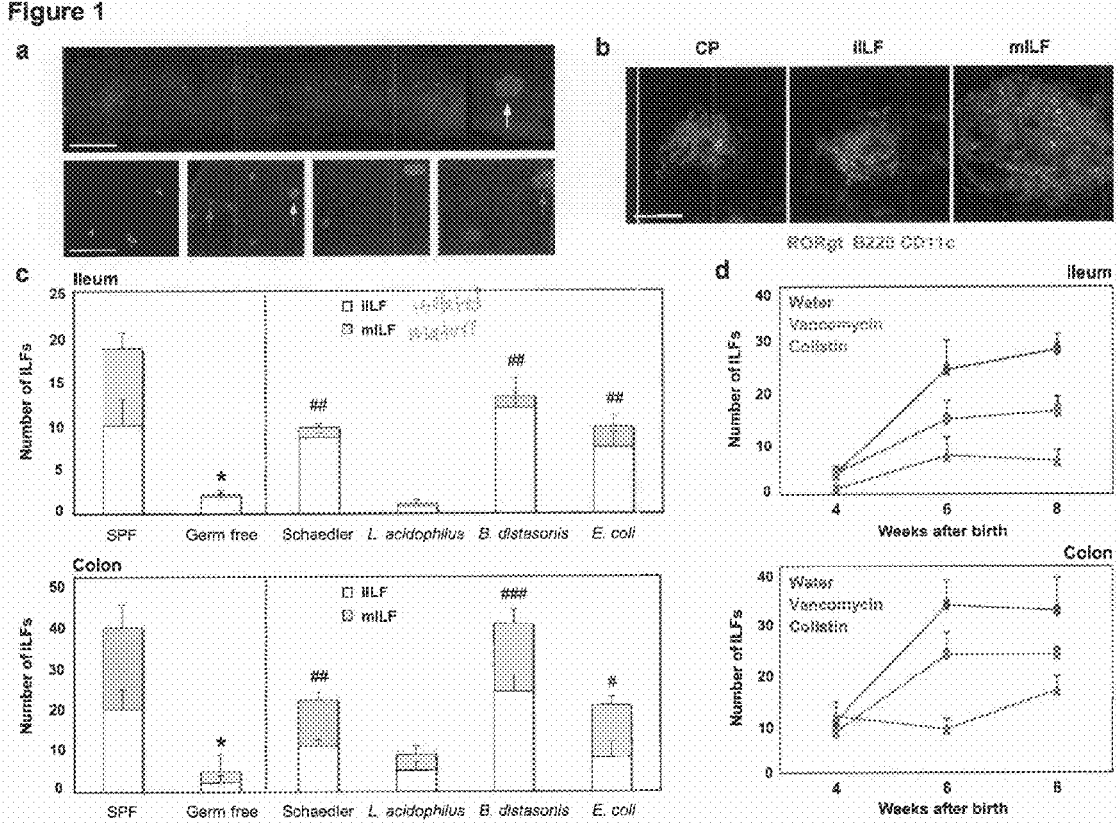
FIG. 1(a)-(d). Intestinal commensal gram-negative bacteria induce an extensive network of isolated lymphoid follicles. a, The network of CPs and ILFs in the ileum of Rorc(γt)-Gfp$^{TG}$ mice. The upper right panel shows a PP (white arrow) at the same magnification. The lower panels show, from left to right, proximal to distal regions of the small intestine. Arrows point to a CP (green), an immature ILF (iILF) (yellow) and a mature ILF (mILF) (red). Scale bar, 2.5 mm (upper panels) or 500 μm (lower panels). b, A CP, a small iILF and a large mILF in sections from the ileum of a Rorc(□t)-Gfp$^{TG}$ mouse were stained as indicated. Scale bar, 60 μm. c, Quantification of ILFs in specific pathogen-free (SPF), germ free mice, or mice reconstituted with the Altered Schaedler's Flora (Supplementary FIG. 2), *Lactobacillus acidophilus, Bacteroides distasonis* or *Escherichia coli*. At least 3 mice per group were analyzed. Error bars, s.d.*P<0.001, unpaired t test, total numbers of ILFs as compared to SPF mice. #P<0.05, ##P<0.01, ##P<0.001, as compared to germ free mice. d, ILFs in SPF mice of the indicated age that were treated from birth with the indicated antibiotics in drinking water. At least 3 mice per group were examined.

Interesting probiotics include *E. coli* strain Nissle 1917, which strongly induces hBD2 in intestinal epithelial cells[29] and should therefore activate the CP-ILF system. Similarly, with the aim of using commensal bacteria or bacteria-derived compounds to treat intestinal disease, Mazmanian, et al showed recently that a polysaccharide derived from the commensal *Bacteroides fragilis* effectively modulates intestinal inflammation[30]. Interestingly, bacteria of the *Bacteroides* genus also induce the formation of ILFs (FIG. 1c).

EXAMPLES

Example 1

Materials and Methods

Example 1 describes the materials and methods used in Examples 2 ff. The methods and materials referred to in Example 1 and the other examples by citation to particular references are specifically incorporated by reference to the pertinent subject matter described by each cited reference.

Mice

BAC-transgenic Rorc(γt)-Gfp$^{TG}$ mice were generated as described previously[31]. The coding sequence for EGFP, including the stop codon, was inserted into exon 1 of Rorc(γt) in place of the endogenous ATG translation start codon, on a 200 kb BAC (Invitrogen) carrying at least 70 kb of sequence upstream of the Rorc(γt) translation start site. Germfree mice of the C3H/HeOrl background (CDTA, Orléans) were bred and maintained at the Institut Pasteur. MyD88-, TRIF-, TLR2- or TLR4-deficient mice were obtained from Dr. S. Akira and backcrossed at least for 8 generations into C57/B16J background. NOD1 (card4$^{-/-}$)-deficient mice were generated by Millennium Pharmaceuticals, and NOD2- (card15$^{-/-}$) deficient rice were provided by Dr. J.-P. Hugot. The card15$^{-/-}$ or card4$^{-/-}$ mice were backcrossed 8 generations into C57BL/6J mice[28]. All mice were kept in specific pathogen-free conditions and all animal experiments were approved by the committee on animal experimentation of the Institut Pasteur and by the French Ministry of Agriculture.

Antibodies, Fusion Proteins and Antibiotics

Purified anti-CD11c (HL3) was purchased from BD Biosciences, phycoerythrin (PE)-, allophycocyanin (APC)- or biotin-conjugated anti-CD45R/B220 (RA3-6B2), and anti-CD45.2 (104) were purchased from eBiosciences, and purified anti-GFP (A-11122) and FITC-conjugated anti-rabbit polyclonal were purchased from Invitrogen. Neutralizing anti-CCL20 (114906) antibody was purchased from R&D Systems and 50-100 µg was injected i.p. in PBS twice a week. Human IgG1 and LTβR-Ig fusion protein have been previously described[12]; 100 µg protein was injected i.p. into pregnant mice 14.5 and 16.5 days after conception, or 50 µg protein was injected i.p. into newborn mice 1 day, 6 days and 12 days after birth, then 100 µg 15 days after birth. Vancomycin and colistin were purchased from Sigma and supplied to mice in the drinking water at a concentration of 500 mg/l and 1 g/l, respectively.

Peptidoglycans

Peptidoglycan were purified from *E. coli* strain MC1061 as previously described[32]. Highly purified PGN (total of 100 mg) was digested with mutanolysin (Sigma)[33] to generate the entire range of muropeptides present in *E. coli* PGN (Supplementary FIG. 3b). Soluble muropeptides were separated by reverse phase HPLC, and the N-acetylglucosamyl-β1,4-N-acetylmuramyl-L-alanyl-D-γ-glytamyl-meso-diaminopimelate-D-alanine (GMtetraDAP) was collected and purity tested by a new HPLC analysis (Supplementary FIG. 3b). The nature of the GMtetraDAP was confirmed by MALDI-TOF mass spectrometry analysis as previously described[33]. Muramyldipeptide (MDP) was purchased from Sigma. Mice received MDP or GMtetraDAP in drinking water at a fixed concentration of 1 µM from the age of 2 weeks (Experiment I) or form birth (experiment II) for different periods of time.

Bacterial Strains and Culture

Figure 2:
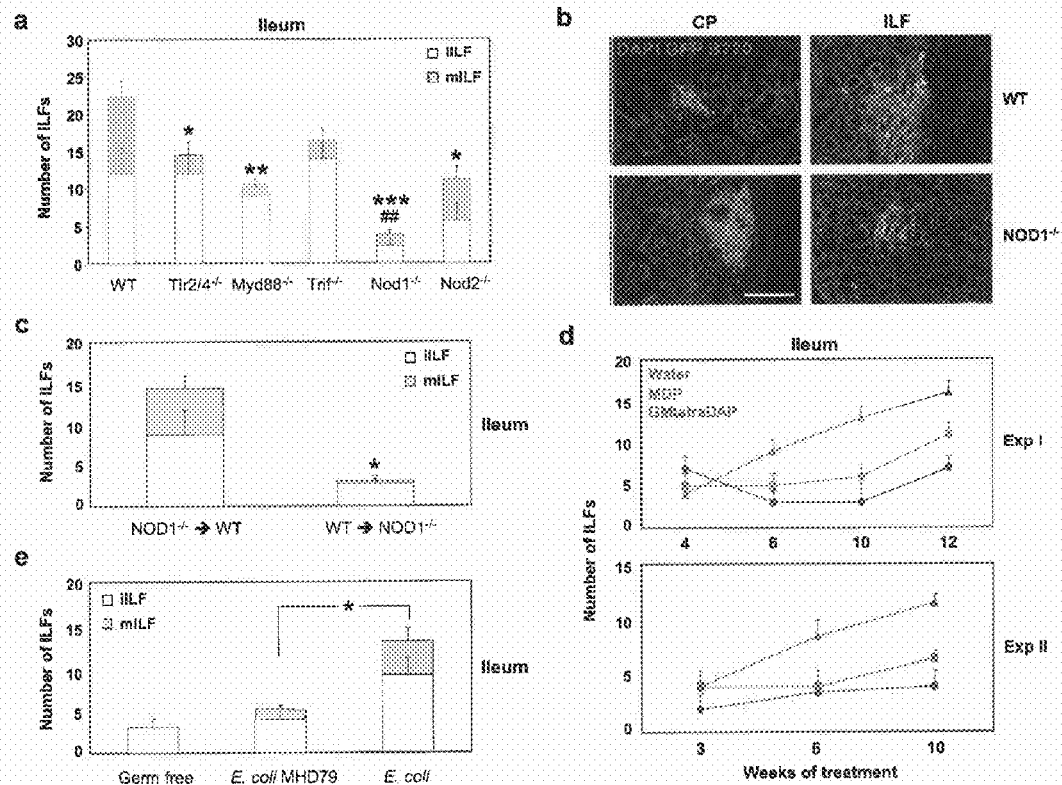
FIG. 2(a)-(e). Peptidoglycans recognized by NOD1 induce the formation of ILFs. a, The number of iILFs and mILFs in the distal ileum of wild type or mutant mice. Error bars, s.d.*P<0.05, P<0.01, *P<0.001, unpaired t test, total number of ILFs as compared to wild type (WT) mice, and ##P<0.01, numbers of iILFs as compared to wild type (WT) mice. b, CPs and ILFs in sections from the ileum of Nod1$^{+/-}$×Rorc(γt)-Gfp$^{TG}$ (WT) mice or Nod1$^{-/-}$×Rorc(γt)-Gfp$^{TG}$ mice were stained as indicated. Scale bar, 125 μm. c, Bone marrow cells from wild type or Nod1$^{-/-}$ mice were adoptively transferred into the liver of irradiated newborn Nod1$^{-/-}$ or wild type hosts, respectively. ILFs were counted 8 weeks after transfer. Error bars, s.d.*P<0.05, unpaired t test, comparing total numbers of ILFs. d, Germfree mice were given MDP or GMtetraDAP in the drinking water from 2 weeks of age (experiment I) or from birth (experiment II), and total ILFs were counted in the distal ileum after different periods of time. e, Adult germfree mice were reconstituted with *E. coli* MC1061 or the mutant *E. coli* MHD79, and ILFs counted 8 weeks later. Error bars, s.d.*P<0.05, unpaired t test, comparing total numbers of ILFs. ILFs were counted in 2-4 mice per group.

ASF bacteria include the Gram$^+$ *Clostridium propionicum* (ASF 356), *Lactobacillus acidophilus* (ASF 360), *Lactobacillus murinus* (ASF 361), *Eubacterium plexicaudatum* (ASF 492) Firmicutes sp. (ASF 500) and *Clostridium* sp. (ASF 502), the Gram$^-$ *Mucispirillum schaedleri* (ASF 457) and *Bacteroides distasonis* (ASF 519) (Supplementary FIG. 2)[13,34], and were obtained from Taconic. The bacteria were cultured in anaerobic conditions on Schaedler agar (Difco laboratories) supplemented with 5% sterile sheep blood (Biorad) in an anaerobic Glove chamber containing a 5% $CO_2$, 10% $H_2$ and 85% $N_2$ atmosphere (Jacomex). The media were pre-reduced by placing them inside the chamber 2 days prior to inoculation of bacteria. Cultures were incubated in the chamber at 37° C. for different periods of time (1-5 days) depending on the bacterial strain. The hexa-mutant of *E. coli* lytic transglycosylase strain MHD79 was derived from the parental strain MC1061 and was previously described[35], and provided by J.-V. Höltje. Strains MC1061 and MHD79 are both streptomycin resistant (selection on LB agar with 100 µg/mL), and strain MHD79 carries additional resistance to chloramphenicol (40 µg/mL), tetracycline (12.5 µg/mL) and kanamycin (50 µg/mL) that allows selective growth. *E. coli* cultures were obtained after 6 h at 37° C. in BHI broth (OD=1 at 600 nm).

Bacterial Colonization of Germfree Mice

Germ-free C3H/HeOrl mice were bred and housed in sterile Trexler isolators. Mice were inoculated at eight weeks of age by intra-gastric and intra-rectal administration of $10^7$-$10^8$ Colony Forming Unit (CFU) of ASF bacteria and *E. coli* as described by the Taconic Technical library available on the world wide web at taconic.com/library. Fecal pellets from inoculated mice were assessed for colonization by microscopic examination of smears and quantified by serial dilutions of stool spread on Schaedler agar plates or by quantitative PCR (qPCR). Colonization of 8 weeks old germ free mice with wild type *E. Coli* (MC1061) or mutant *E. coli* (MHD79) was achieved by intra-gastric administration of $10^9$ CFU of bacteria. Bacterial status was checked every week. Fresh stool from each group were re-suspended in peptone broth and the suspensions were spread onto two series of LB agar plates supplemented with and without streptomycin (100 µg/ml) to distinguish the *E. coli* strains from any other potential contaminant, or on LB agar plates supplemented with kanamycin (50 µg/ml), a specific marker of strain MHD79. Mice were colonized to similar levels by strains MC1061 and MHD79 (~2.5×10⁹ cfu/g of feces) and analyzed 8 weeks after bacterial reconstitution.

Quantitative Analysis of Commensal Bacteria

The whole ileum and colon were cut longitudinally. After removal of intestinal contents, the tissues were vigorously washed several times in PBS. The supernatants from these washes were used to quantify the bacterial content of the intestinal biofilm. DNA was extracted as described previously[36]. Quantitative PCR for 16S rDNA was performed on a Lightcycler apparatus (Roche) and normalized to total DNA. Absolute numbers of bacteria were determined from standard curves established by qPCR of serial dilutions of reference plasmids harboring the 16S rDNA gene from each of the ASF strains. All reactions were performed in 10 µl reactions using the Quantitect SYBR green (Quiagen™). Primers, reaction conditions and quantification have been adapted from three previous studies[37-39].

Generation of Chimeric Mice

Bone marrow cells were isolated from C57BL/6 or Nod1$^{-/-}$ adult mice and treated with RBC buffer (Gibco™) to eliminate red blood cells. A total of 3×10⁶ cells in 25 µl of PBS were injected into the liver of C57BL/6 or Nod1$^{-/-}$ newborn mice that were previously irradiated at 400 rads. Reconstituted mice were sacrificed and analyzed 8 weeks after transfer.

Immunofluorescence Histology

Intestines were opened and washed several times in PBS before fixation overnight at 4° C. in a fresh solution of 4% paraformaldehyde (Sigma) in PBS. The samples were then washed 1 day in PBS, incubated in a solution of 30% sucrose (Sigma) in PBS until the samples sank, embedded in OCT compound 4583 (Sakura Finetek), frozen in a bath of isopentane cooled with liquid nitrogen and stocked at –80° C. Frozen blocs were cut at 8 µm thickness arid sections collected onto Superfrost/Plus slides (VWR). Slides were dried 1 hour and processed for staining, or stocked at –80° C. For staining, slides were first hydrated in PBS-XG, (PBS containing 0.1% triton X-100 and 1% normal bovine serum, VWR) for 5 min and blocked with 10% bovine serum in PBS-XG for 1 hour at room temperature. Endogenous biotin was blocked with a biotin blocking kit (Vector Laboratories). Slides were then incubated with primary polyclonal Ab or conjugated mAb (in general 1/100) in PBS-XG overnight at 4° C., washed 3 times 5 min with PBS-XG, incubated with secondary conjugated polyclonal Ab or streptavidin for 1 hour at room temperature, washed once, incubated with 4'6-diamidino-2-phenylindole-2HCl (DAPI) (Sigma) 5 min at room temperature, washed 3 times 5 min and mounted with Fluoromount-G (Southern Biotechnology Associates). Slides were examined under an Axiolmager M1 fluorescence microscope (Zeiss) equipped with a CCD camera and images were processed with Axio Vision software (Zeiss). For the quantification of CPs and ILFs, 10-20 sections were cut at regular intervals through the whole thickness of flat ileal or colonic fragments of 2 cm in length and stained. CPs and ILFs were then counted under a fluorescence microscope.

Laser Capture Microdissection

Embryos or organs were embedded in OCT compound 4583 (Sakura Finetek), frozen in a bath of isopentane cooled with liquid nitrogen and stocked at –80° C. Frozen blocs were cut at 10 µm thickness and serial sections collected onto Superfrost/Plus slides (VWR). Sections were immediately fixed 5 min in acetone at –20° C., dried and stored at –80° C., or thawed and immediately stained for 5 sec with Histogen (Molecular Devices), washed briefly in RNase-free water supplemented with ProtectRNA (Sigma), dehydrated successively in one bath of 70% ethanol for 30 sec, two bathes of 95% ethanol for 1 min, two bathes of water-free ethanol (VWR) for 2 min, and two bathes of xylene for 5 min and air-dried. Slides were transferred immediately into a Veritas Laser Capture Microdissector (Molecular Devices), and the regions of interest were microdissected and captured with Capsure Macro LCM caps (Molecular Devices). RNA was isolated using the Picopure RNA Isolation kit (Molecular Devices), and its quality assessed using the 2100 Bioanalyzer system (Agilent Technologies).

Gene Expression Analysis 250-500 pg of high quality total RNA was subjected to one linear mRNA amplification cycle using the MessageBooster Kit for qRT-PCR (Epicentre Biotechnologies). 50-100 ng of amplified mRNA was then converted to cDNA using Superscript III (Invitrogen). All procedures were performed according to the manufacturer's protocols. Real time PCR was performed using specific primers pairs (SuperArray Bioscience Corporation) on a PTC-200 thermocycler equipped with a Chromo4 detector (Bio-Rad Laboratories). Additioral primer pairs specific for Defb3 message were tested[40]. Data was analyzed using Opticon Monitor software (Bio-Rad Laboratories).

Example 2

Visualization of CPs and ILFs

Fetal LTi cells and LTi-like cells in CPs express the nuclear hormone receptor RORγt, which is required for the generation of LTi and CP cells and the development of secondary lymphoid tissues and ILFs[2,6,10]. The extensive network of CPs and ILFs was visualized in transgenic mice expressing the enhanced green fluorescent protein EGFP under control of the Rorc(γt) locus (Rorc(γt)-Gfp$^{TG}$ mice) on a bacterial artificial chromosome (BAC) (FIG. 1a). CPs contain mostly RORγt⁺ LTi cells and a smaller population of dendritic cells (DCs)[6], whereas ILFs constitute a continuum of structures harboring increasing numbers of B cells (FIG. 1b)[5], previously grouped into immature ILFs (iILFs) that harbor relatively few B cells, and mature ILFs (mILFs) that form an organized B cell follicle[11]. As shown in Supplementary FIG. 1a, the number of CPs was highest in the proximal intestine, whereas ILFs, in particular mILFs, were most prominent in the distal ileum and the colon correlating with the increasing bacterial density towards the distal segments of the intestine.

Furthermore, whereas CPs develop independently of germs[4] starting the second week after birth (Supplementary FIG. 1b), the development of ILFs required bacteria (FIG. 1c) and occurred around the weaning age of 2-3 weeks (Supplementary FIG. 1b), during a boost in bacterial input provided by solid food.

In germfree mice, only CPs or ILFs harboring few B cells were found[1,8]. The development of CPs and the subsequent formation of ILFs was blocked by administration, during the first 2 weeks after birth, of lymphotoxin β receptor (LTβR)-Ig fusion protein (Supplementary FIG. 1c,d), an antagonist of lymphoid tissue development[12], demonstrating the developmental relationship between CPs and ILFs.

Example 3

ILF Formation

In order to identify which component of the intestinal flora induces the formation of ILFs, adult germfree mice were first reconstituted with a cocktail of bacterial strains including *E. coli* and members of the Altered Schaedler's Flora (ASF) (Supplementary FIG. 2), derived the normal commensal bacterial flora[13]. After 8 weeks, significant numbers of ILFs were found in the ileum and the colon (FIG. 1c), demonstrating that a restricted set of commensal bacteria species, devoid of invasive bacteria or pathogens, can induce the formation of ILFs. In these experimental conditions however, ileal ILFs failed to mature to the same extent as in normal specific pathogen-free (SPF) animals, suggesting that additional commensal microorganisms are required for full maturation, or that the experimental colonization protocol used here in adult mice does not fully replicate natural colonization occurring in the ileum of newborn animals.

Example 4

Induction of ILFs using Gram-Negative Bacteria

The inventors assessed whether individual ASF species were sufficient to induce the formation of ILFs. Reconstitution of germfree mice with the Gram$^+$ *Lactobacillus acidophilus* induced no or few ILFs, whereas reconstitution with the Gram$^-$ *Bacteroides distasonis* or *Escherichia coli* induced high numbers of ileal and colonic ILFs (FIG. 1c). To confirm that Gram-negative commensals have a major impact on the formation of ILFs, normal SPF mice were treated from birth with antibiotics that target preferentially Gram$^+$ (vancomycin) or Gram$^-$ (colistin) bacteria (FIG. 1d). Similar to germfree mice, mice treated with colistin formed few ILFs.

In contrast, mice treated with vancomycin formed significant numbers of ILFs, but lower numbers than in control mice, suggesting some role for Gram$^+$ bacteria in the formation of ILFs, for example through activation of NOD2 and TLRs (see below), or some level of toxicity of vancomycin on Gram-negative bacteria. Together, these results demonstrate a dominant role for commensal Gram-negative bacteria in the formation of ILFs and suggest involvement of receptors of microbe-associated molecular patterns (MMAPs).

Example 5

NOD1-Deficient Mice have Significantly Reduced Numbers of ILFs

Figure 3:
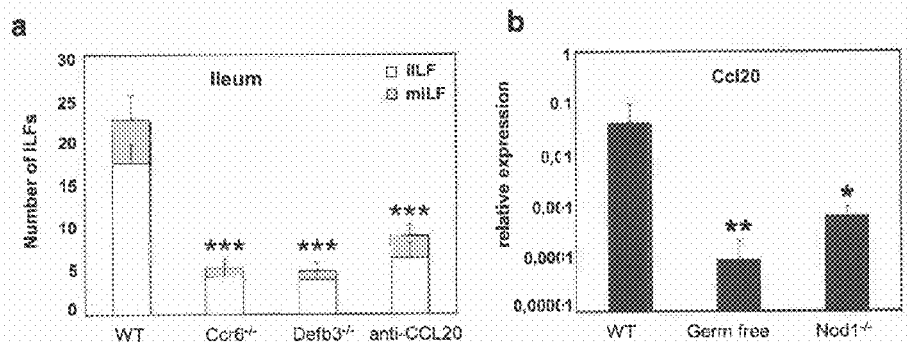
FIGS. 3(a) and (b). A critical role for CCR6 ligands in the formation of ILFs. a, The number of iILFs and mILFs were counted in the distal ileum of CCR6$^{-/-}$ or Defb3$^{-/-}$ (mBD3-deficient) mice, or mice injected with neutralizing anti-CCL20 antibody. ILFs were counted in 3-4 mice per group. b, Expression of transcripts coding for CCL20 in intestinal epithelium of wild type, germfree or Nod1$^{-/-}$ mice. Total epithelium or the crypt regions were isolated by laser capture microdissection (Supplementary FIG. 6) and processed for RNA extraction. Results from duplicate PCR runs and two mice were normalized to the amplification of Gadph transcripts. Error bars, s.d.*P<0.05, P<0.01, *P<0.001, unpaired t test, total numbers of ILFs or relative transcript expression, as compared to wild type mice.

In view of these results, the inventors investigated whether members of the TLR family and their associated signaling pathways, as well as members of the NOD-like receptor family, were involved in the formation of ILFs. In the ileum and the colon of TLR2/4-, Myd88-, TRIF- or NOD2-deficient mice, maturation of ILFs was incomplete but induction of iILF formation was not significantly altered (FIG. 2a and Supplementary FIG. 3a). Thus TLRs and NOD2 appeared to be involved in the maturation of ILFs rather than in the induction of ILF formation. In accordance with this observation, TLRs activate the NF-κB pathway and induce the expression of inflammatory mediators such as TNF, required for the maturation of mILFs, but not for the induction of iILFs[11].

In contrast, both the number of iILFs and mILFs were significantly reduced in the ileum of NOD1-deficient mice (FIG. 2a), whereas CPs were hypertrophic (FIG. 2b). In the colon of NOD1-deficient mice, few iILFs were found whereas mILFs were hypertrophic (Supplementary FIG. 3a,b). Thus NOD1, recognizing PGNs derived from Gram-negative bacteria[14], was required for the generation of ileal iILFs, in accordance with these findings that Gram-negative commensals were required in this process (FIG. 1c,d). Furthermore, using bone marrow chimeras, the inventors determined that NOD1 expression by stromal cells such as epithelial cells, but not hematopoietic cells such as DCs and macrophages, were necessary for the generation of ileal ILFs (FIG. 2c). In the colon, the absence of NOD1 clearly affected ILF induction and maturation, but the large colonic flora appeared to induce ILFs also through pathways redundant with NOD1.

Example 6

NOD1 Ligands Induce ILF formation

The inventors also determined whether a ligand for NOD1 derived from Gram-negative bacteria, such as the muropeptide GMtetraDAP (N-acetylglucosamyl-β1,4-N-acetylmuramyl-L-alanyl-D-γ-glytamyl-meso-diaminopimelate-D-alanine) or its anhydro derivative also known as tracheal cytotoxin (TCT) (Supplementary FIG. 4)[15], could induce the formation of ILFs.

Germfree mice were fed with GMtetraDAP or the NOD2 ligand muramyl-dipeptide (MDP) in their drinking water for different periods of time. GMtetraDAP, but not MDP, induced a significant number of ILFs, mostly iILFs, in the ileum after 6 weeks of treatment (FIG. 2d and Supplementary FIG. 5a). Significant numbers of ILFs were also detected in the colon after 10 weeks of treatment with GMtetraDAP starting from birth (Supplementary FIG. 3c, Experiment II).

Furthermore, when germfree mice where reconstituted with an *E. coli* mutant (MHD79) that released low amounts of PGNs, containing mainly GMtetraDAP and TCT, as compared to wild type *E. coli* MC1061, the induction of ILFs was abrogated (FIG. 2e and Supplementary FIG. 5b), demonstrating the essential role of NOD1 ligands in the induction of ILF formation by Gram-negative bacterial commensals. Our finding that commensal bacteria, or TCT, induce the genesis of intestinal lymphoid tissues is reminiscent of the formation of the light-emitting organ in the squid *Euprymna scolopes*[16]. Colonization of internal crypts by luminescent bacteria *Vibrio fischeri* induces hemocytes (the invertebrate macrophages) infiltration of the crypts, epithelial apoptosis and morphogenesis, a process that is recapitulated by TCT alone. The squid molecule recognizing TCT remains however to be identified.

Example 7

CCR6 Ligands CCL20/MIP-3-α and β-Defensin 3/mBD3 Induce ILFs

ILFs fail to form in mice deficient for the chemokine receptor CCR6 (FIG. 3a)[17], shown to be required on B cells and expressed by LTi-like cells in CPs[18]. CCR6 has two known ligands, CCL20 (or MIP-3α), which is highly expressed by the follicle-associated epithelium (FAE) overlaying PPs[19] and ILFs (data not shown), as well as in ILFs[18], and β-defensin 3 (mBD3)[20], which is expressed by inflamed epithelia and intestinal crypts[21]. Interestingly, activation of NOD1 induces expression of hBD2, the human ortholog of mBD3, in a panel of human epithelial cell lines[22,23], and the expression of mBD4, another mouse ortholog of hBD2, is impaired in NOD1-deficient mice[24]. In mBD3-deficient mice, we found as few ILFs as in CCR6-deficient mice (FIG. 3a), demonstrating that mBD3 is required to induce the formation of ILFs, presumably through activation of its receptor CCR6. Furthermore, blocking CCL20 with neutralizing antibody also significantly reduced ILF formation, showing that the two CCR6 ligands have non-redundant roles in the activation of the CP-ILF system.

Example 8

Commensal Bacterial Induce Expression of CCL20 through NOD1

Crypts were isolated from the ileum of germfree or NOD1-deficient mice by laser capture microdissection (LCM) (Supplementary FIG. 6) and transcripts (Defb3) coding for mBD3 or CCL20 were quantified by qRT-PCR. Whereas Defb3 transcripts could not be detected by our method in crypts or in total intestinal epithelial cells, CCL20 transcripts were clearly detected and were substantially decreased in crypts isolated from germfree or NOD1-deficient mice (FIG. 3b), indicating that commensals induced the expression of CCL20 through NOD1.

Together, these data suggest that the detection of bacterial commensals through NOD1 induces the expression of mBD3 and CCL20, which both activate CCR6 and induce the formation of iILFs. In patients, defectives production of hBD2 predisposes to Crohn's disease[25], possibly both as direct and indiret consequences of the bactericidal and ILF-inducing activities of hBD2, respectively.

Example 9

Profound Flora Alterations in Animals Lacking NOD1, mBD3 and/or ILFs

Finally, we measured the feedback impact of the CP-ILF system on the bacterial commensals. The bacterial biofilm of the ileum was collected from wild-type, NOD1- or mBD3-deficient mice, as well as from mice treated with LTβR-Ig fusion protein that lacked ILFs but developed a normal set of LNs and PPs (Supplementary FIG. 1c). Quantitative PCR was performed on bacterial 16S rDNA using primers targeting the whole bacterial kingdom, or major groups of intestinal bacterial commensals (Supplementary Table 1). In both NOD1- and mBD3-deficient mice, the total bacterial population was expanded a 100-fold, and in LTβ R-Ig-treated mice, this expansion was 10-fold (FIG. 4a,b). Specifically, the important groups of commensals Clostridiales and Bacteroides[9] and the smaller group of Enterobacteriaceae expanded a 100-fold in NOD1-deficient mice and 10- to 100-fold in ILF-deficient mice, reminiscent of the results obtained in AID-deficient mice that do not produce IgA[9]. A small expansion of segmented filamentous bacteria (SFB), related to Clostridiales and potent inducers of PP function[26], was observed in NOD1-deficient mice. In mBD3-deficient mice, the Gram-Bacteroides and Enterobacteriaceae expanded, in accordance with the antimicrobial activity of the human ortholog hBD-2 against gram-negative bacteria[27]. On the other hand, the gram-positive Lactobacillaceae were reduced in all three types of mice, and Clostridiales failed to expand in mBD3-deficient mice that also lack ILFs, even though this group expanded in ILF-deficient mice. The individual ASF strains (Supplementary FIG. 2) followed, in general, the behavior of their corresponding bacterial group (Supplementary FIG. 7). However, some exceptions underscore the complexity of behaviors of individual species or groups of bacteria in response to alterations both in the intestinal immune system and in the composition of the bacterial community. Together, these data show profound alterations in the bacterial flora of the ileum of mice that lack NOD1, mBD3 and/or ILFs, and demonstrate the role of the CP-ILF system in intestinal bacterial homeostasis. However, as expected, the absence of NOD1 or mBD3 had a stronger impact on the total bacterial flora than the specific absence of ILFs in LTβR-Ig-treated mice, as in addition to decreased ILF formation, NOD1-[28] or mBD3-deficient mice have immune defects that directly impact on the bacterial flora, such as a decreased production of antimicrobial peptides in NOD1-deficient mice[24].

Modifications and Other Embodiments

Various modifications and variations of the described products, compositions and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the immunological, medical, biological, chemical or pharmacological arts or related fields are intended to be within the scope of the following claims.

INCORPORATION BY REFERENCE

Each document, patent, patent application or patent publication cited by or referred to in this disclosure is incorporated by reference in its entirety. Bouskra, et al., Nature 456(7221): 507-10 (2008) is incorporated by reference in its entirety, especially with regard to specific mechanisms for lymphoid tissue genesis induced via NOD1 and its specific description of FIGS. 5-11 herein. herein. Specific subject matter, such as specific methods or materials, is specifically incorporated by reference to the pertinent sections of the cited references as is conventional ill the art. However, no admission is made that any such reference constitutes background art and the right to challenge the accuracy and pertinence of the cited documents is reserved.

REFERENCES

1. Hamada, H. et al. Identification of multiple isolated lymphoid follicles on the antimesenteric wall of the mouse small intestine. *J. Immunol* 168, 57-64 (2002).
2. Tsuji, M. et al. Requirement for lymphoid tissue-inducer cells in isolated follicle formation and T cell-independent immunoglobulin a generation in the gut. *Immunity* 29, 261-271 (2008).
3. Mebius, R. E. Organogenesis of lymphoid tissues. *Nat Rev Immunol* 3, 292-303 (2003).
4. Kanamori, Y. et al. Identification of novel lymphoid tissues in murine intestinal mucosa where clusters of c-kit$^+$ IL-7R$^+$ Thay1$^+$ lympho-hemopoietic progenitors develop. *J Exp Med* 184, 1449-1459 (1996).
5. Pabst, O. et al. Cryptopatches and isolated lymphoid follicles: dynamic lymphoid tissues dispensable for the generation of intraepithelial lymphocytes. *Eur J Immunol* 35, 98-107 (2005).
6. Eberl, G. & Littman, D. R. Thymic origin of intestinal αβ T cells revealed by fate mapping of RORγt$^+$ cells. *Science* 305, 248-251 (2004).
7. Eberl, G. Inducible lymphoid tissues in the adult gut: recapitulation of a fetal developmental pathway? *Nat Rev Immunol* 5, 413-420 (2005).

8. Pabst, O. et al. Adaptation of solitary intestinal lymphoid tissue in response to microbiota and chemokine receptor CCR7 signaling. *J Immunol* 177, 6824-6832 (2006).
9. Fagarasan, S. et al. Critical roles of activation-induced cytidine deaminase in the homeostasis of gut flora. *Science* 298, 1424-1427 (2002).
10. Eberl, G. et al. An essential function for the nuclear receptor RORγt in the generation of fetal lymphoid tissue inducer cells. *Nat Immunol* 5, 64-73 (2004).
11. Lorenz, R. G., Chaplin, D. D., McDonald, K. G., McDonough, J. S. & Newberry, R. D. Isolated lymphoid follicle formation is inducible and dependent upon lymphotoxin-sufficient B lymphocytes, lymphotoxin γ receptor, and TNF receptor I function. *J Immunol* 170, 5475-5482 (2003).
12. Rennert, P. D., Browning, J. L., Mebius, R., Mackay, F. & Hochman, P. S. Surface lymphotoxin α/β complex is required for the development of peripheral lymphoid organs. *J Exp Med* 184, 1999-2006 (1996).
13. Dewhirst, F. E. et al. Phylogeny of the defined murine microbiota: altered Schaedler flora. *Appl Environ Microbiol* 65, 3287-3292 (1999).
14. Fritz, J. H., Ferrero, R. L., Philpott, D. J. & Girardin, S. E. Nod-like proteins in immunity, inflammation and disease. *Nat Immunol* 7, 1250-1257 (2006).
15. Magalhaes, J. G. et al. Murine Nod1 but not its human orthologue mediates innate immune detection of tracheal cytotoxin. *EMBO Rep* 6, 1201-1207 (2005).
16. Koropatnick, T. A. et al. Microbial factor-mediated development in a host-bacterial mutualism. *Science* 306, 1186-1188 (2004).
17. Lugering, A. & Kucharzik, T. Induction of intestinal lymphoid tissue: the role of cryptopatches. *Ann N Y Acad Sci* 1072, 210-217 (2006).
18. McDonald, K. G. et al. CC chemokine receptor 6 expression by B lymphocytes is essential for the development of isolated lymphoid follicles. *Am J Pathol* 170, 1229-1240 (2007).
19. Tanaka, Y. et al. Selective expression of liver and activation-regulated chemokine (LARC) in intestinal epithelium in mice and humans. *Eur J Immunol* 29, 633-642 (1999).
20. Yang, D. et al. Beta-defensins: linking innate and adaptive immunity through dendritic and T cell CCR6. *Science* 286, 525-528 (1999).
21. Bals, R. et al. Mouse beta-defensin 3 is an inducible antimicrobial peptide expressed in the epithelia of multiple organs. *Infect Immun* 67, 3542-3547 (1999).
22. Voss, E. et al. NOD2/CARD15 mediates induction of the antimicrobial peptide human beta-defensin-2. *J Biol Chem* 281, 2005-2011 (2006).
23. Uehara, A., Fujimoto, Y., Fukase, K. & Takada, H. Various human epithelial cells express functional Toll-like receptors, NOD1 and NOD2 to produce anti-microbial peptides, but not proinflammatory cytokines. *Mol Immunol* 44, 3100-3111 (2007).
24. Boughan, P. K. et al. Nucleotide-binding oligomerization domain-1 and epidermal growth factor receptor: critical regulators of beta-defensins during Helicobacter pylori infection. *J Biol Chem* 281, 11637-11648 (2006).
25. Wehkamp, J. et al. Inducible and constitutive beta-defensins are differentially expressed in Crohn's disease and ulcerative colitis. *Inflamm Bowel Dis* 9, 215-223 (2003).
26. Talham, G. L., Jiang, H. Q., Bos, N. A. & Cebra, J. J. Segmented filamentous bacteria are potent stimuli of a physiologically normal state of the murine gut mucosal immune system. *Infect Immun* 67, 1992-2000 (1999).
27. Schroder, J. M. & Harder, J. Human β-defensin-2. *Int J Biochem Cell Biol* 31, 645-651 (1999).
28. Fritz, J. H. et al. Nod1-mediated innate immune recognition of peptidoglycan contributes to the onset of adaptive immunity. *Immunity* 26, 445-459 (2007).
29. Wehkamp, J. et al. NF-kappaB- and AP-1-mediated induction of human beta defensin-2 in intestinal epithelial cells by *Escherichia coli* Nissle 1917: a novel effect of a probiotic bacterium. *Infect Immun* 72, 5750-5758 (2004).
30. Mazmanian, S. K., Round, J. L. & Kasper, D. L. A microbial symbiosis factor prevents intestinal inflammatory disease. *Nature* 453, 620-625 (2008).
31. Lochner, M. et al. In vivo equilibrium of proinflammatory IL-17+ and regulatory IL-10+ Foxp3+ RORγt+ T cells. *J Exp Med* 205, 1381-1393 (2008).
32. Girardin, S. E. et al. Nod1 detects a unique muropeptide from gram-negative bacterial peptidoglycan. *Science* 300, 1584-1587 (2003).
33. Antignac, A. et al. Detailed structural analysis of the peptidoglycan of the human pathogen Neisseria meningitidis. *J Biol Chem* 278, 31521-31528 (2003).
34. Schaedler, R. W. & Dubos, R. J. The fecal flora of various strains of mice. Its bearing on their susceptibility to endotoxin. *J Exp Med* 115, 1149-1160 (1962).
35. Heidrich, C., Ursinus, A., Berger, J., Schwarz, H. & Holtje, J. V. Effects of multiple deletions of murein hydrolases on viability, septum cleavage, and sensitivity to large toxic molecules in *Escherichia coli*. *J Bacteriol* 184, 6093-6099 (2002).
36. Godon, J. J., Zumstein, E., Dabert, P., Habouzit, F. & Moletta, R. Molecular microbial diversity of an anaerobic digestor as determined by small-subunit rDNA sequence analysis. *Appl Environ Microbiol* 63, 2802-2813 (1997).
37. Barman, M. et al. Enteric salmonellosis disrupts the microbial ecology of the murine gastrointestinal tract. *Infect Immun* 76, 907-915 (2008).
38. Sarma-Rupavtarm, R. B., Ge, Z., Schauer, D. B., Fox, J. G. & Polz, M. F. Spatial distribution and stability of the eight microbial species of the altered schaedler flora in the mouse gastrointestinal tract. *Appl Environ Microbiol* 70, 2791-2800 (2004).
39. Ge, Z. et al. Colonization dynamics of altered Schaedler flora is influenced by gender, aging, and Helicobacter hepaticus infection in the intestines of Swiss Webster mice. *Appl Environ Microbiol* 72, 5100-5103 (2006).
40. Rivas-Santiago, B. et al. β-Defensin gene expression during the course of experimental tuberculosis infection. *J Infect Dis* 194, 697-701 (2006).

The invention claimed is:

1. A method for modulating intestinal homeostasis by generating adaptive lymphoid tissue comprising:

administering to a subject in need thereof who is a neonate, a subject with a naïve immune system, or a subject who has a reduced number of ILFs prior to treatment due to an innate immune defect compared to a normal subject, an agent that is an NOD1 (nucleotide oligomerization domain 1) ligand that is an isolated or purified gram-negative peptidoglycan removed from other components of a gram-negative bacterium or an isolated or purified muropeptide obtained from said gram-negative peptidoglycan in an amount sufficient to induce or enhance the formation of ILFs (isolated lymphoid follicles) in said subject compared to a control subject not receiving said NOD1 (nucleotide oligomerization domain 1) ligand.

2. The method of claim 1, wherein said agent comprises isolated or purified gram-negative peptidoglycan obtained from E. coli.

3. The method of claim 1, wherein said agent comprises isolated or purified gram-negative peptidoglycan obtained from E. coli strain MC1061.

4. The method of claim 1, comprising administering an agent that is meso-diaminopimelic acid-type peptidoglycan.

5. The method of claim 1, wherein said agent is muropeptide N-acetylglucosamyl-β1,4-N-acetylmuramyl-L-alanyl-D-γ-glytamyl-meso-diaminopimelate-D-alanine.

6. The method of claim 1, wherein said subject is a neonate or a subject with a naïve immune system.

7. The method of claim 1, wherein said subject in need thereof has an innate immune defect where IgA is not produced or where defective IgA is produced.

8. The method of claim 1, wherein said subject in need thereof has an innate immune defect where defective secretory antibodies are produced or where defective secretory components are produced.

9. The method of claim 1, wherein said subject has been treated with or exposed to an agent that disrupts intestinal flora or reduces the number of ILFs.

10. The method of claim 1, wherein said subject has been exposed to a chemical agent, drug, or antibiotic that alters the microbial flora in the intestines or infected by a microbe causing disruption of microbial flora and/or enteric disease.

11. The method of claim 1, wherein said subject has gastroenteritis or diarrhea.

12. The method of claim 1, wherein said subject has undergone gastrointestinal surgery, bariatric surgery, or appendectomy.

13. The method of claim 1 that comprises administering an isolated or purified gram-negative peptidoglycan removed from other components of a gram-negative bacterium.

14. The method of claim 1 that comprises administering an isolated or purified muropeptide obtained from a gram-negative peptidoglycan.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Primer UniF340.  Group: Bacteria;  all genera
```

-continued

```
<400> SEQUENCE: 1
actcctacgg gaggcagcag t                                              21

<210> SEQ ID NO 2
<211> LENGTH: 18
<212> TYPE: DNA
<213> ORGANISM: Artificial Sequence
<220> FEATURE:
<223> OTHER INFORMATION: Primer UniR514;  Clostridiales

<400> SEQUENCE: 2
attaccgcgg ctgctggc                                                  18

<210> SEQ ID NO 3
<211> LENGTH: 18
<212> TYPE: DNA
<213> ORGANISM: Artificial Sequence
<220> FEATURE:
<223> OTHER INFORMATION: Primer UniF338

<400> SEQUENCE: 3
actcctacgg gaggcagc                                                  18

<210> SEQ ID NO 4
<211> LENGTH: 23
<212> TYPE: DNA
<213> ORGANISM: Artificial Sequence
<220> FEATURE:
<223> OTHER INFORMATION: Primer C.cocR491

<400> SEQUENCE: 4
gcttcttagt caggtaccgt cat                                            23

<210> SEQ ID NO 5
<211> LENGTH: 21
<212> TYPE: DNA
<213> ORGANISM: Artificial Sequence
<220> FEATURE:
<223> OTHER INFORMATION: Primer SFB736F

<400> SEQUENCE: 5
gacgctgagg catgagagca t                                              21

<210> SEQ ID NO 6
<211> LENGTH: 22
<212> TYPE: DNA
<213> ORGANISM: Artificial Sequence
<220> FEATURE:
<223> OTHER INFORMATION: Primer SFB844R

<400> SEQUENCE: 6
gacggcacgg attgttaatt ca                                             22

<210> SEQ ID NO 7
<211> LENGTH: 19
<212> TYPE: DNA
<213> ORGANISM: Artificial Sequence
<220> FEATURE:
<223> OTHER INFORMATION: Primer LabF362

<400> SEQUENCE: 7
agcagtaggg aatcttcca                                                 19

<210> SEQ ID NO 8
<211> LENGTH: 17
```

```
<212> TYPE: DNA
<213> ORGANISM: Artificial Sequence
<220> FEATURE:
<223> OTHER INFORMATION: Primer LabR677

<400> SEQUENCE: 8
caccgctaca catggag                                                    17

<210> SEQ ID NO 9
<211> LENGTH: 20
<212> TYPE: DNA
<213> ORGANISM: Artificial Sequence
<220> FEATURE:
<223> OTHER INFORMATION: Primer BactF285

<400> SEQUENCE: 9
ggttctgaga ggaaggtccc                                                 20

<210> SEQ ID NO 10
<211> LENGTH: 18
<212> TYPE: DNA
<213> ORGANISM: Artificial Sequence
<220> FEATURE:
<223> OTHER INFORMATION: Primer UniR338

<400> SEQUENCE: 10
gctgcctccc gtaggagt                                                   18

<210> SEQ ID NO 11
<211> LENGTH: 19
<212> TYPE: DNA
<213> ORGANISM: Artificial Sequence
<220> FEATURE:
<223> OTHER INFORMATION: Primer Uni515F

<400> SEQUENCE: 11
gtgccagcag ccgcggtaa                                                  19

<210> SEQ ID NO 12
<211> LENGTH: 23
<212> TYPE: DNA
<213> ORGANISM: Artificial Sequence
<220> FEATURE:
<223> OTHER INFORMATION: Primer Ent826R

<400> SEQUENCE: 12
gcctcaaggg cacaacctcc aag                                             23
```